United States Patent
Pan et al.

(10) Patent No.: US 11,578,060 B2
(45) Date of Patent: Feb. 14, 2023

(54) JAK3 SELECTIVE INHIBITOR

(71) Applicant: PEKING UNIVERSITY SHENZHEN GRADUATE SCHOOL, Shenzhen (CN)

(72) Inventors: Zhengying Pan, Shenzhen (CN); Liyang Shi, Shenzhen (CN); Xitao Li, Shenzhen (CN)

(73) Assignee: PEKING UNIVERSITY SHENZHEN GRADUATE SCHOOL, Shenzhen (CN)

( * ) Notice: Subject to any disclaimer, the term of this patent is extended or adjusted under 35 U.S.C. 154(b) by 6 days.

(21) Appl. No.: 17/059,211

(22) PCT Filed: May 30, 2019

(86) PCT No.: PCT/CN2019/089213
§ 371 (c)(1),
(2) Date: Nov. 26, 2020

(87) PCT Pub. No.: WO2019/228442
PCT Pub. Date: Dec. 5, 2019

(65) Prior Publication Data
US 2021/0214344 A1    Jul. 15, 2021

(30) Foreign Application Priority Data
May 30, 2018 (CN) .......................... 201810535993.0

(51) Int. Cl.
| | | |
|---|---|---|
| C07D 401/14 | (2006.01) | |
| C07D 403/14 | (2006.01) | |
| C07D 471/04 | (2006.01) | |
| A61P 37/06 | (2006.01) | |
| C07D 207/448 | (2006.01) | |

(52) U.S. Cl.
CPC ............ *C07D 403/14* (2013.01); *A61P 37/06* (2018.01); *C07D 207/448* (2013.01); *C07D 401/14* (2013.01); *C07D 471/04* (2013.01)

(58) Field of Classification Search
CPC ... C07D 401/14; C07D 403/14; C07D 471/04
See application file for complete search history.

(56) References Cited

FOREIGN PATENT DOCUMENTS

| CN | 1478087 A | 2/2004 |
| CN | 1639153 A | 7/2005 |
| WO | 2005/068455 A1 | 7/2005 |

OTHER PUBLICATIONS

Shi, Liyang et al., "Discovery of an Orally Available Janus Kinase 3 Selective Covalent Inhibitor", J. Med. Chem., vol. 62, No. (2), Jan. 7, 2019 (Jan. 7, 2019), pp. 1054-1066.

Thoma, G. et al., "Identification of a Potent Janus Kinase 3 inhibitor with High Selectivity within the Janus Kinase Family", Journal of Medicinal Chemistry, vol. 54, No. (1), Dec. 14, 2010 (Dec. 14, 2010), pp. 284-288.
International Search Report of PCT Application No. PCT/CN2019/089213, dated Aug. 26, 2019.
Yang Zhimin et al., "Design and synthesis of (aza)indolyl maleimide-based covalent inhibitors of glycogen synthase kinase 3[beta]", Organic & Biomolecular Chemistry, vol. 16, No. 22, Jan. 1, 2018 (Jan. 1, 2018), pp. 4127-4140, XP55836237, ISSN: 1477-0520, DOI: 10.1039/C80B00642C * tables 1 and 2 *.
The extended European search report for the corresponding EP application No. 19809988.9 dated Sep. 10, 2021.

*Primary Examiner* — Brian E McDowell
(74) *Attorney, Agent, or Firm* — Jun He Law Offices P.C.; James J. Zhu

(57) ABSTRACT

The present invention relates to a compound of Formula (I)/(II) or pharmaceutically acceptable salts thereof. In Formula (I), Rh, Rg, Rf, m, Re, Rd, Ra, Rb, and Rc are as defined in the description. The present invention further relates to a pharmaceutical composition comprising the compound of Formula (I)/(II) or pharmaceutically acceptable salts thereof, and use of the compound of Formula (I)/(II) or the pharmaceutical composition in the manufacture of a medicament for treating inflammations such as rheumatoid arthritis.

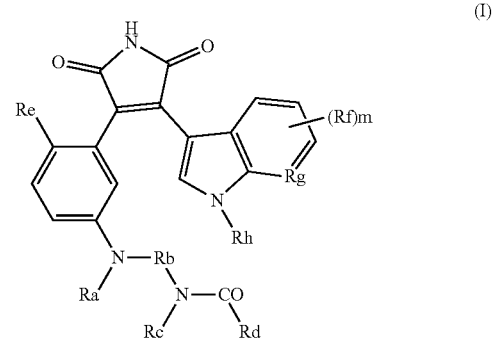

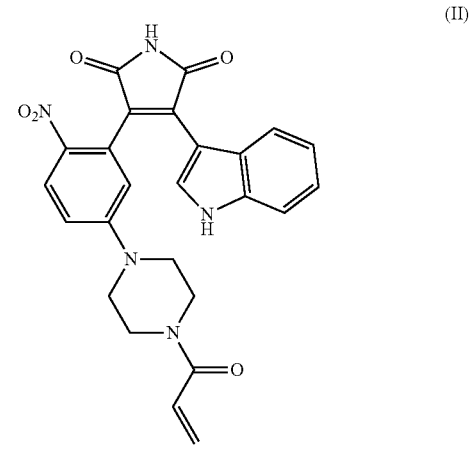

20 Claims, 6 Drawing Sheets

JAK3 SELECTIVE INHIBITOR

CROSS-REFERENCE TO RELATED APPLICATIONS

This application is a national stage application under 35 U.S.C. § 371 of International Application No. PCT/CN2019/089213, filed May 30, 2019, which claims the benefit of priority to Chinese Application No. 201810535993.0, filed May 30, 2018, the contents of each of which applications are incorporated herein by reference in their entireties.

FIELD OF THE INVENTION

The present invention relates to JAK3 selective inhibitors.

BACKGROUND

JAK kinases (JAKs) and their downstream effectors, signal transducer and activator of transcription (STATs), are essential for T cell signal transduction. The JAK family has four members, JAK1, JAK2, JAK3 and TYK2, which bind to cytokine receptors in pairs and participate in regulation of cytokine-mediated signal pathways. JAK3 paired with JAK1 binds to cytokine receptors containing γ-common chains, and is involved in signal transduction of interleukins IL-2, IL-4, IL-7, IL-9, IL-15, IL-21, etc. In contrast to other JAKs, which are broadly expressed, JAK3 is only expressed in the hematopoietic system. Therefore, it was generally believed that selective inhibition of JAK3 could achieve safe and effective immune effects.

Tofacitinib, an approved drug developed by Pfizer, which was initially developed as a selective JAK3 inhibitor, but was later discovered that Tofacitinib also had high inhibitory activity against JAK1 and was actually a non-selective JAKs inhibitor.

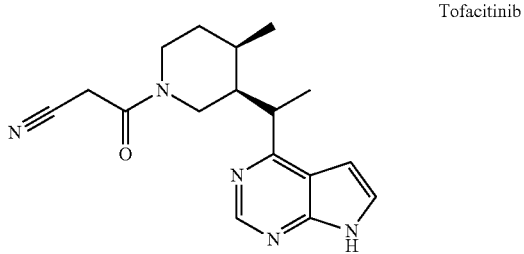 [SMILES: CC(c1ncnc2[nH]ccc12)[C@H]1CN(C(=O)CC#N)CC[C@H]1C]

Tofacitinib

Although had similar inhibitory activity to Tofacitinib at the level of enzymatic activity, the highly selective JAK3 inhibitor NIBR3049, which was developed by Novartis, was significantly less potent than Tofacitinib in the aspect of intracellular inhibitory activity against phosphorylation of a downstream substrate STAT5.

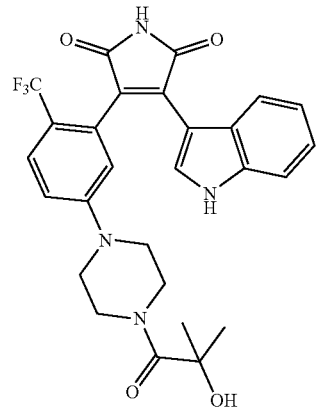

NIBR3049

During the recent years, highly selective JAK3 inhibitors have been obtained by covalently targeting Cys909, a unique cysteine residue of JAK3, including PF-06651600 developed by Pfizer, which is currently under Phase II clinical research.

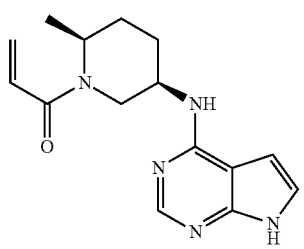

PF-06651600

There is still an urgent need in the art for a JAK3 selective inhibitor with high enzymatic activity and cellular activity.

SUMMARY OF THE INVENTION

One of the objectives of the present invention is to provide a JAK3 selective inhibitor with biological activity.

In one aspect, the present invention provides a compound (including stable isotope substitutes thereof) of Formula I or a pharmaceutically acceptable salt thereof,

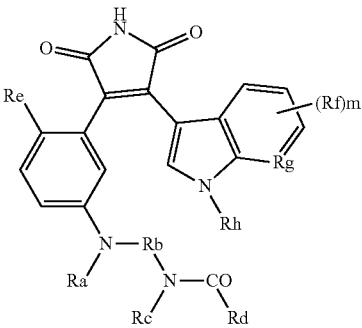

Formula I wherein,
Rh is H or methyl, preferably H;
Rg is CH, —C—Rf or N, preferably CH;

Rf is a substituent, preferably selected from methyl or halogen (such as F, Cl, Br or I);

m is 0, 1, 2 or 3, preferably 0 or 1, more preferably 0;

Re is an electron-withdrawing group selected from the group consisting of tertiary amine cations (—N$^+$R'$_3$, wherein R' is independently selected from H and $C_1$-$C_6$ alkyl), nitro (—NO$_2$), trihalomethyl (—CX$_3$, X=F, Cl, Br or I), halogen (such as F, Cl, Br and I), formyl (—CHO), acyl (—CO—$C_{1-4}$ alkyl), carboxyl (—COOH), cyano (—CN), sulfonic acid group (—SO$_3$H);

Rd is alkenyl or alkynyl, for example, having 2, 3, 4, 5 or 6 carbon atoms;

Ra, Rb and Rc are selected from the following combinations:

(1) Rb is $C_1$-$C_4$ alkylene (e.g. $C_1$-$C_3$ alkylene, such as methylene, ethylidene, 1,3-propylidene), and Ra and Rc are hydrogen or $C_1$-$C_6$ alkyl (e.g. $C_1$-$C_4$ alkyl, such as methyl, ethyl, n-propyl, isopropyl, n-butyl, tert-butyl);

(2) Rb is $C_1$-$C_4$ alkylene (e.g. $C_1$-$C_3$ alkylene, such as methylene, ethylidene, 1,3-propylidene), and Ra and Rc are attached together to form $C_2$-$C_4$ alkylene (e.g. $C_2$-$C_3$ alkylene, such as ethylidene, 1,3-propylidene);

(3) Ra is hydrogen or $C_1$-$C_6$ alkyl (e.g. $C_1$-$C_4$ alkyl, such as methyl, ethyl, n-propyl, isopropyl, n-butyl, tert-butyl), and Rb and Rc together with the N atom to which they are attached form a 5- or 6-membered saturated heterocyclic ring containing a N atom;

(4) Rc is hydrogen or $C_1$-$C_6$ alkyl (e.g. $C_1$-$C_4$ alkyl, such as methyl, ethyl, n-propyl, isopropyl, n-butyl, tert-butyl), and Ra and Rb together with the N atom to which they are attached form a 5- or 6-membered saturated heterocyclic ring containing a N atom.

In one aspect, the present invention provides a compound (including stable isotope substitutes thereof) of Formula II or a pharmaceutically acceptable salt thereof:

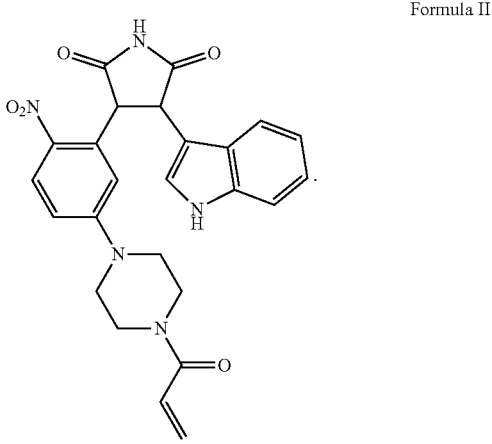 [SMILES: C=CC(=O)N1CCN(c2ccc([N+](=O)[O-])c(C3C(=O)NC(=O)C3c3c[nH]c4ccccc34)c2)CC1]

Formula II

In one aspect, the present invention provides a pharmaceutical composition comprising the compound of Formula I (including stable isotope substitutes thereof) or a pharmaceutically acceptable salt thereof, or the compound of Formula II (including stable isotope substitutes thereof) or a pharmaceutically acceptable salt thereof, and a pharmaceutically acceptable carrier. The pharmaceutically acceptable carrier includes inert solid fillers or excipients and sterile aqueous solutions or organic solutions. The compounds should be present in the pharmaceutical composition in an amount sufficient to provide the desired dosage. The techniques of formulating and administering the compounds disclosed in the present invention are well known to those skilled in the art, which, for example, can be found in *Remington: the Science and Practice of Pharmacy*, 19$^{th}$ edition, Mack Publishing Company, Easton, Pa. (1995).

In one aspect, the present invention provides use of the compound of Formula I (including stable isotope substitutes thereof) or a pharmaceutically acceptable salt thereof, the compound of Formula II (including stable isotope substitutes thereof) or a pharmaceutically acceptable salt thereof, or the pharmaceutical composition of the present invention in the manufacture of a medicament for treating inflammations such as rheumatoid arthritis.

In one aspect, the present invention provides a compound of Formula I or Formula II (including stable isotope substitutes thereof) as a JAK3 selective inhibitor.

DETAILED DESCRIPTION

Definition of Abbreviations

Figure 1:
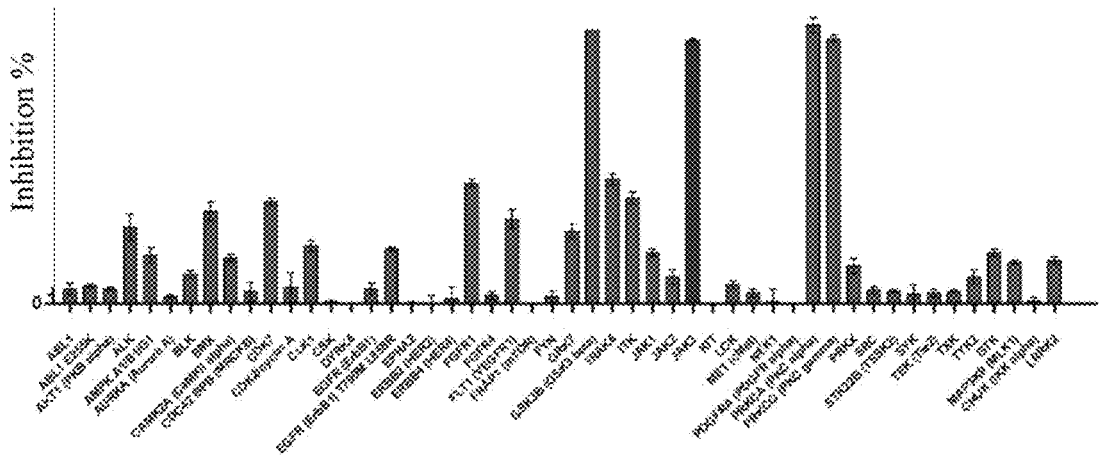
FIG. 1: selectivity assay results of compounds against a panel of kinases.

Ala: alanine
ATP: adenosine triphosphate
AUC: area under the curve
Boc: tert-butoxycarbonyl
BTK: Bruton's tyrosine kinase
CDI: 1,1'-carbonyldiimidazole
Cys: cysteine
DCM: dichloromethane
DIEA: N,N-diisopropyethyllamine
DMF: dimethyl formamide
DMSO: dimethyl sulfoxide
EGFR: epidermal growth factor receptor
GSK3β: glycogen synthase kinase 3-β
HTRF: homogeneous time-resolved fluorescence
IL-2: interleukin-2
IL-6: interleukin-6
IL-15: interleukin-15
IFN-α: interferon-α
ITK: interleukin-2 inducible T cell kinase
JAK: janus kinase
JAK3: janus kinase 3
Leu: leucine
LPS: lipopolysaccharide
Lys: lysine
MCP-1: monocyte chemotactic protein 1
Met: methionine
PBMC: peripheral blood mononuclear cell
PBS: phosphate-buffered saline
PE: petroleum ether
PK: pharmacokinetics
PKC: protein kinase C
RA: rheumatoid arthritis RT (or rt): room temperature
STAT: signal transducer and activator of transcription
TFA: trifluoroacetic acid
THF: tetrahydrofuran
Val: valine
HATU: 1-[Bis(dimethylamino)methylene]-1H-1,2,3-triazolo[4,5-b]pyridinium 3-oxidhexafluorophosphate
Pd$_2$(dba)$_3$: tris(dibenzylideneacetone)dipalladium(0)
JohnPhos: 2-(di-tert-butylphosphino)biphenyl
RuPhos: 2-dicyclohexylphosphino-2',6'-diisopropoxybiphenyl.

The compounds were prepared according to Schemes I, II, III or IV as follows.

-continued

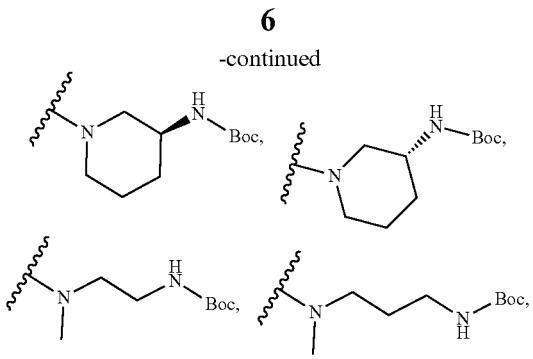

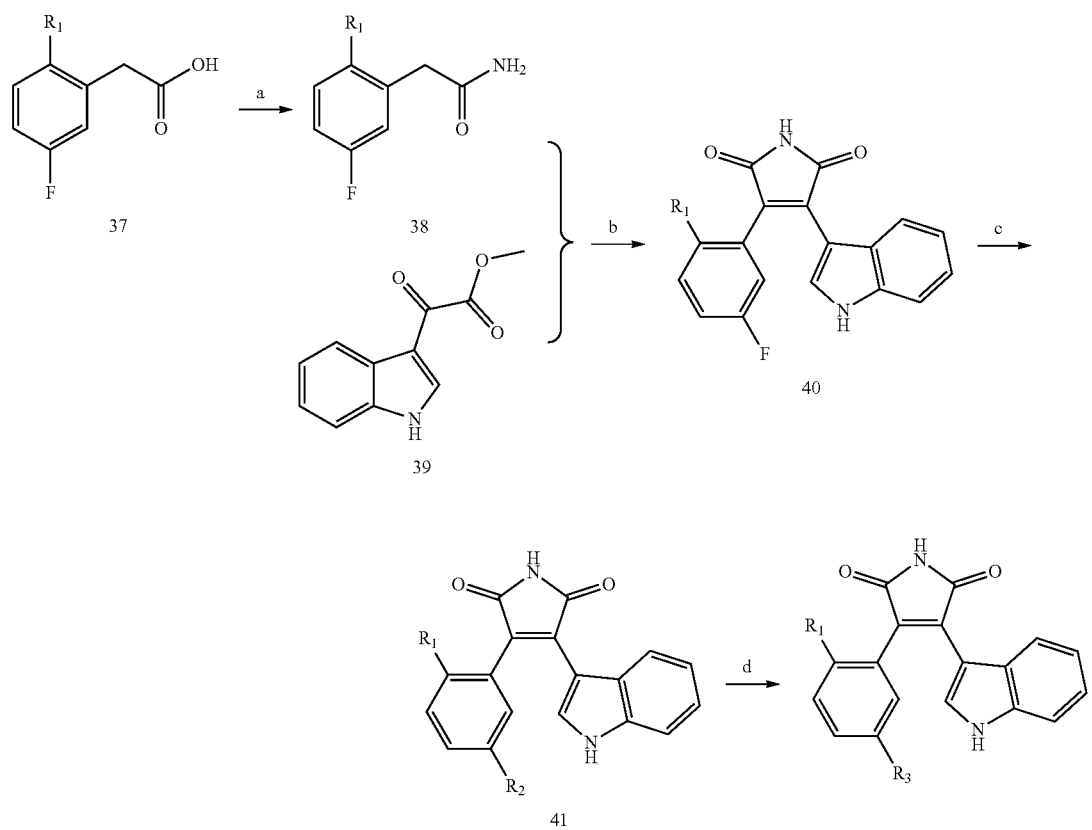

wherein,
R$_1$ is selected from CF$_3$ and NO$_2$;
R$_2$ is selected from

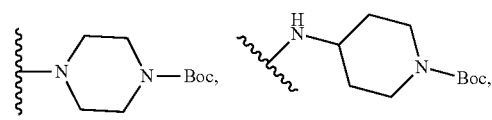

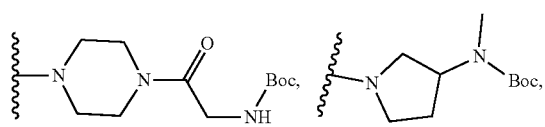

-continued

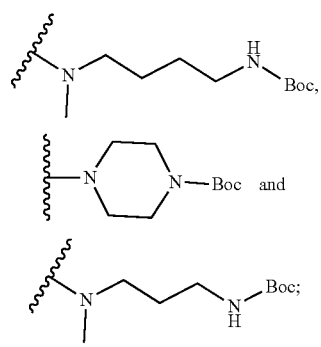

R₃ is selected from

[chemical structures of R₃ substituents including various piperazine, piperidine, pyrrolidine, and amine-linked acrylamide/acrylate groups]

Reaction Reagents and Main Conditions:
(a) i) CDI, DMF, rt, about 0.5 hour;
   ii) NH₃ (7N) in MeOH, rt, about 1 hour;
(b) ᵗBuOK, THF, 0° C.-10° C., about 45 minutes;
(c) Boc-protected piperazine or amines, DMSO, 150° C., overnight;
(d) i) TFA/DCM, rt, about 15 minutes;
   ii) acryloyl chloride/DIEA, THF, H₂O, 0° C. to rt, about 10 minutes, or carboxylic acid, HATU, DIEA, DMF.

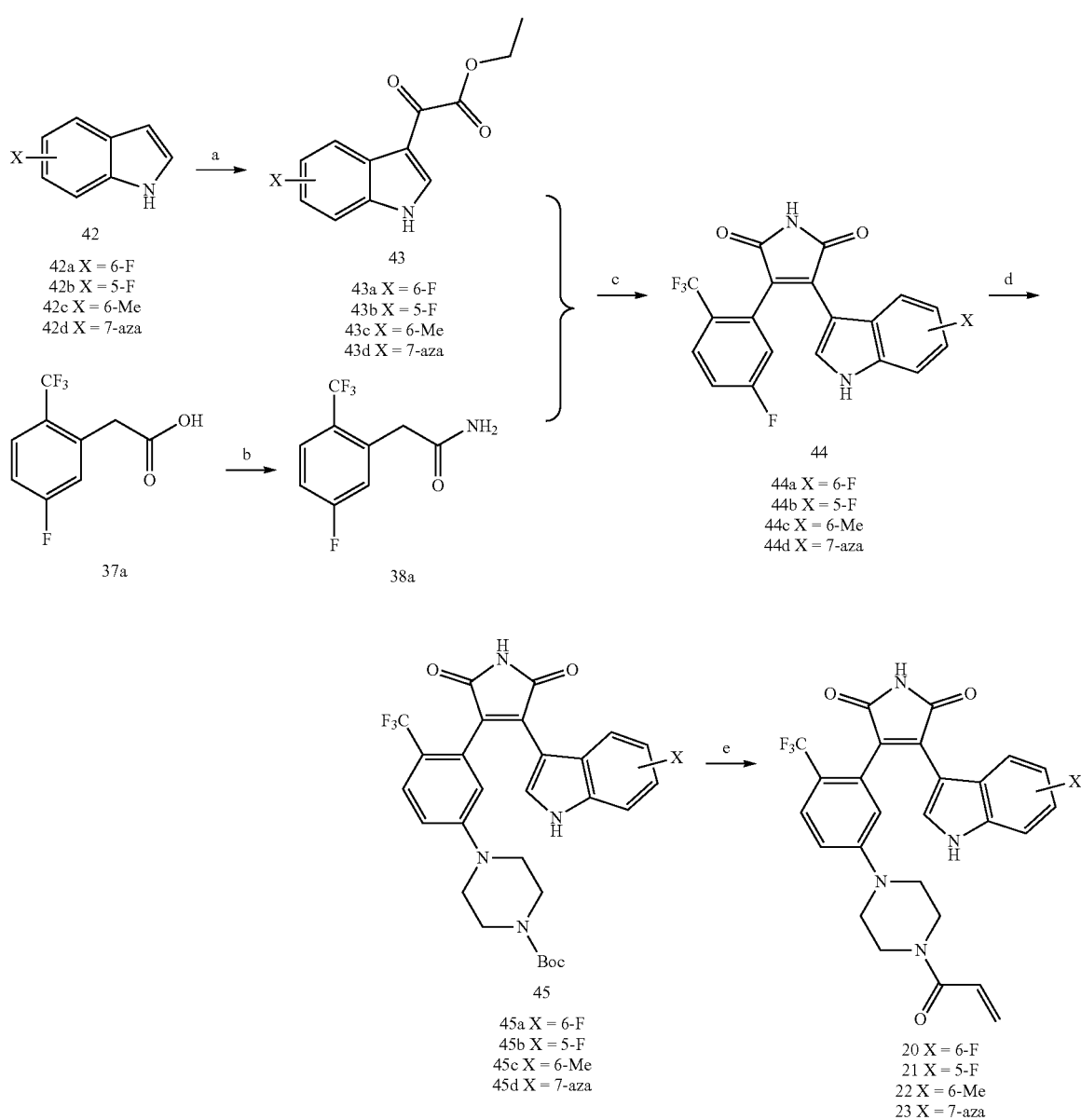

Scheme II

Reaction Reagents and Main Conditions:

(a) ethyl 2-chloro-2-oxoacetate, Et$_2$AlCl, DCM, about 2 hours, 0° C.;

(b) i) CDI, DMF, rt, about 0.5 hour;
   ii) NH$_3$ (7N) in MeOH, rt, about 1 hour;

(c) $^t$BuOK, THF, 0° C. to 10° C., about 45 minutes;

(d) Boc-protected piperazine, DMSO, 150° C., overnight;

(e) i) TFA/DCM, rt, about 15 minutes,
   ii) acryloyl chloride/DIEA, THF, H$_2$O, 0° C. to rt, about 10 minutes.

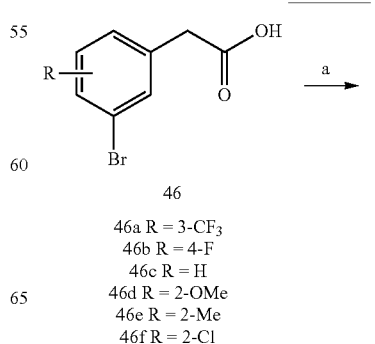

Scheme III

46a R = 3-CF$_3$
46b R = 4-F
46c R = H
46d R = 2-OMe
46e R = 2-Me
46f R = 2-Cl

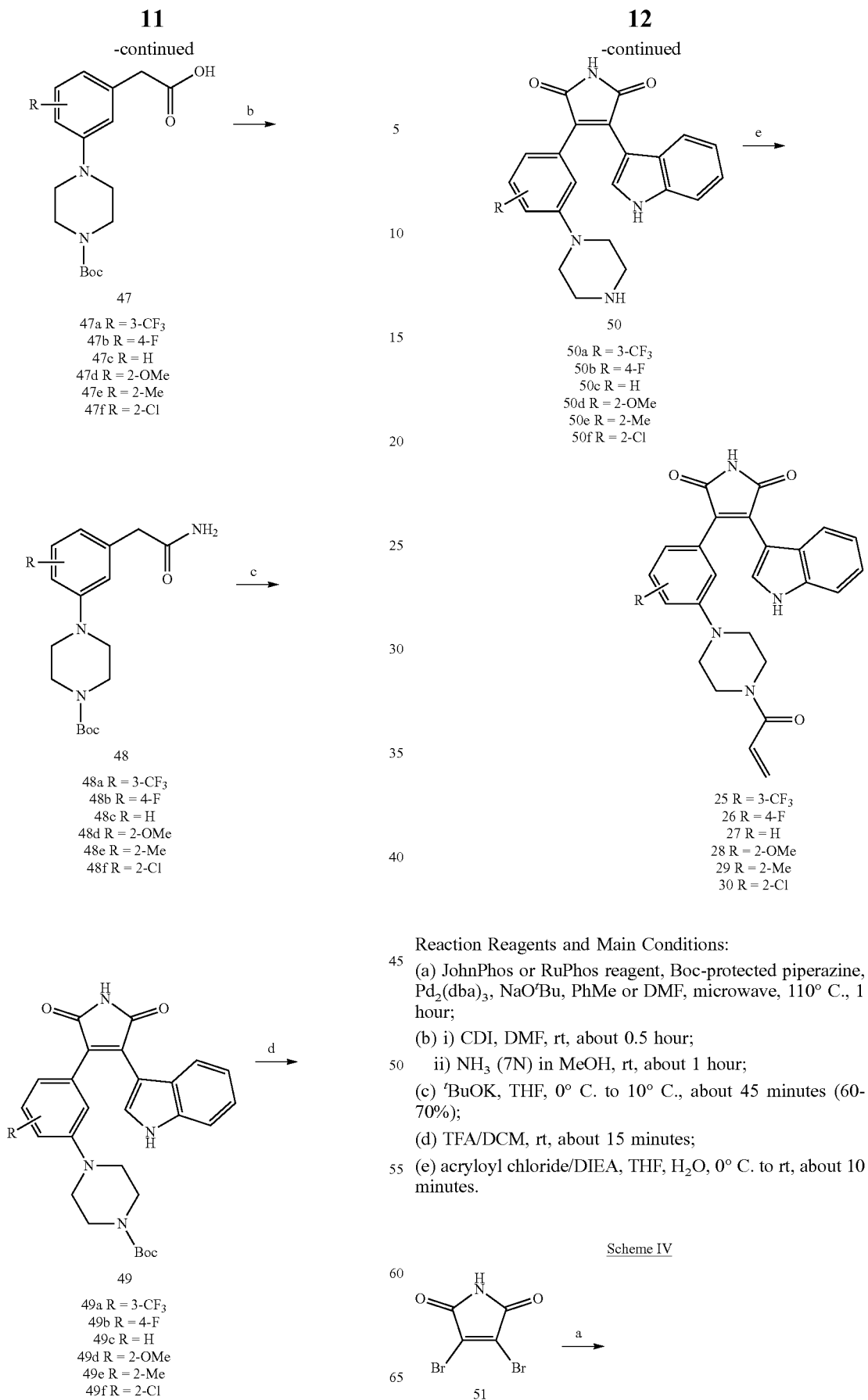

13

-continued

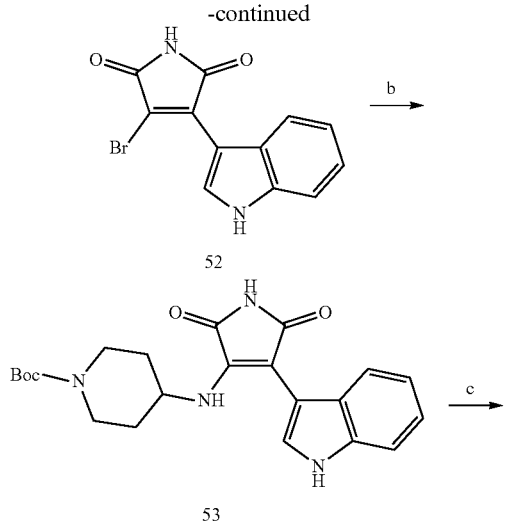

14

-continued

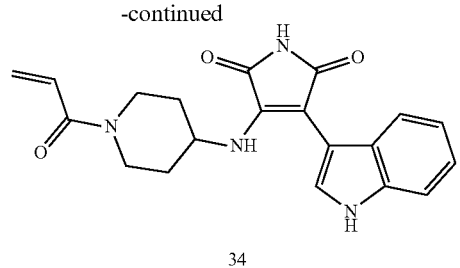

Reaction Reagents and Main Conditions:
(a) indole, EtMgBr in Et$_2$O, THF, reflux, about 1 hour;
(b) Boc-protected amine, DIEA, DMSO, 100° C.;
(c) (i) TFA/DCM, rt, about 15 minutes;
(ii) acryloyl chloride/DIEA, THF, H$_2$O, 0° C. to rt, about 10 minutes.

Table: Compound Structures and IC$_{50}$ Values

| No. | R | Preparation Scheme | IC$_{50}$ (nM) $K_{m\ ATP}$ | 1 nM |
|---|---|---|---|---|
| 5 | piperazine-acryloyl | I | 1.5 | 520 |
| 6 | 4-aminopiperidine-acryloyl | I | 6.4 | 3456 |
| 7 | piperazine-glycinamide-acryloyl | I | 41 | ND |
| 8 | N-methyl-pyrrolidine-acrylamide | I | 4.4 | ND |
| 9 | (S)-3-aminopiperidine-acryloyl | I | 21 | >30000 |

-continued

Table: Compound Structures and IC$_{50}$ Values

| No. | Structure | Scheme | K$_{m\,ATP}$ | 1 nM |
|---|---|---|---|---|
| 10 | (piperidine with NHC(O)CH=CH$_2$) | I | 21 | 3690 |
| 11 | (N-methyl-N-(2-acrylamidoethyl)) | I | 0.6 | ND |
| 12 | (N-methyl-N-(3-acrylamidopropyl)) | I | 0.6 | 1276 |
| 13 | (N-methyl-N-(4-acrylamidobutyl)) | I | 16 | ND |

| No. | R | Scheme | K$_{m\,ATP}$ | 1 nM |
|---|---|---|---|---|
| | | Preparation | IC$_{50}$ (nM) | |
| 14 | –C(O)CH=CH–CH$_2$–N(CH$_3$)$_2$ | I | 21 | ND |
| 15 | –C(O)CH=CHCH$_3$ | I | 104 | ND |
| 16 | –C(O)CH$_2$Cl | I | 0.4 | 210 |
| 17 | –C(O)CH$_2$Br | I | 19 | 709 |

-continued

Table: Compound Structures and IC₅₀ Values

| 18 | ![structure] | I | 0.8 | 212 |

| | Preparation | IC$_{50}$ (nM) | |
|---|---|---|---|
| NO. | R$_1$ | R$_2$ | Scheme | K$_{m\ ATP}$ | 1 nM |
| 19 | 3-CF₃, 4-(piperazinyl-acryloyl)phenyl | 1-methyl-1H-indol-3-yl | | 2.0 | 584 |
| 20 | 3-CF₃, 4-(piperazinyl-acryloyl)phenyl | 6-fluoro-1H-indol-3-yl | II | 2.8 | 817 |
| 21 | 3-CF₃, 4-(piperazinyl-acryloyl)phenyl | 5-fluoro-1H-indol-3-yl | II | 5.4 | 895 |
| 22 | 3-CF₃, 4-(piperazinyl-acryloyl)phenyl | 6-methyl-1H-indol-3-yl | II | 7.5 | 650 |
| 23 | 3-CF₃, 4-(piperazinyl-acryloyl)phenyl | 7-azaindol-3-yl | II | 4.0 | 750 |
| 25 | 3,5-bis(CF₃)-phenyl piperazinyl acryloyl | 1H-indol-3-yl | III | 894 | ND |

-continued
Table: Compound Structures and IC$_{50}$ Values
| 26 | 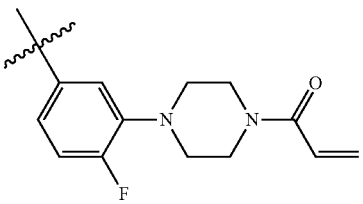 [SMILES: *c1ccc(F)c(N2CCN(C(=O)C=C)CC2)c1] | 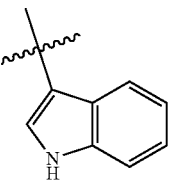 [SMILES: *c1c[nH]c2ccccc12] | III | 873 | ND |
| 27 | 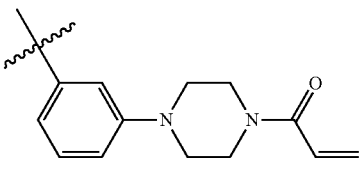 [SMILES: *c1cccc(N2CCN(C(=O)C=C)CC2)c1] | 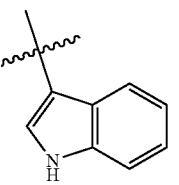 [SMILES: *c1c[nH]c2ccccc12] | III | 232 | ND |
| 28 | 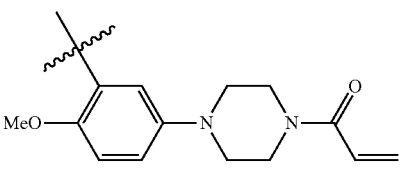 [SMILES: *c1cc(N2CCN(C(=O)C=C)CC2)ccc1OC] | 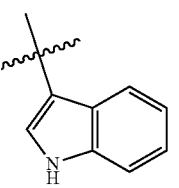 [SMILES: *c1c[nH]c2ccccc12] | III | 52 | ND |
| 29 | 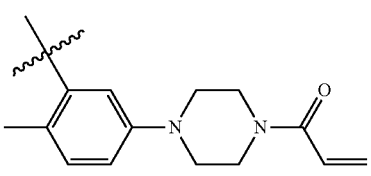 [SMILES: *c1cc(N2CCN(C(=O)C=C)CC2)ccc1C] | 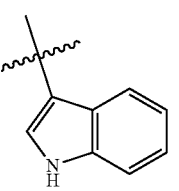 [SMILES: *c1c[nH]c2ccccc12] | III | 21 | ND |
| 30 | 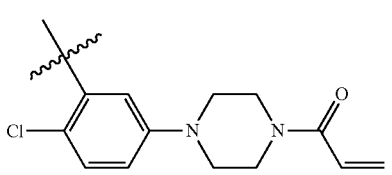 [SMILES: *c1cc(N2CCN(C(=O)C=C)CC2)ccc1Cl] | 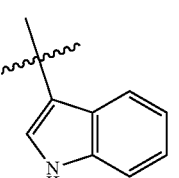 | III | 4.3 | 450 |
| 31 | 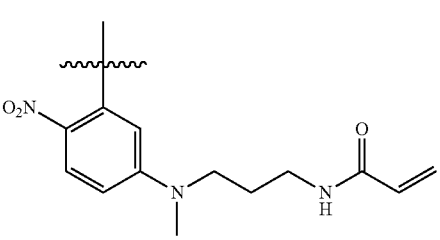 | 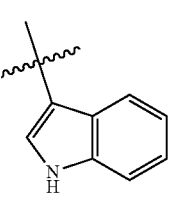 [SMILES: *c1c[nH]c2ccccc12] | I | 0.4 | 332 |
| 32 | 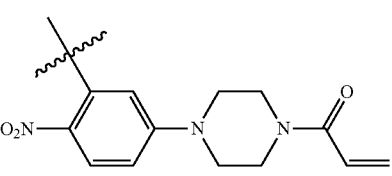 | 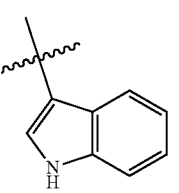 [SMILES: *c1c[nH]c2ccccc12] | I | 0.4 | 80 |
| 33 | 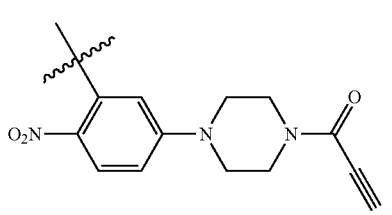 [SMILES: *c1cc(N2CCN(C(=O)C#C)CC2)ccc1[N+](=O)[O-]] | 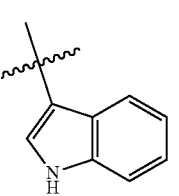 [SMILES: *c1c[nH]c2ccccc12] | I | <0.1 | 90 |

Table: Compound Structures and IC$_{50}$ Values

| | | | | | |
|---|---|---|---|---|---|
| 34 | [structure: N-H piperidine with acryloyl group] | | [indole] | IV | 1777 | ND |
| 35 | [structure: F$_3$C-phenyl-piperazine-propanoyl] | | [indole] | I | 27 | 1000 |
| 36 | [structure: O$_2$N-phenyl-piperazine-propanoyl] | | [indole] | I | 6 | 210 |

The synthesis processes of compounds are described in detail below by referring to Schemes I to IV above and taking Compounds 5, 20, 28, 32, 34 as examples. Other compounds can be prepared in a similar manner with reference to the Schemes I to IV above, which can be easily understood by those skilled in the art.

All reagents were purchased commercially and used without further purification, unless otherwise stated. Solvents were re-evaporated before use. Reactions were monitored by thin-layer silica gel plate (TLC, GF254, 60-F250, 0.2 mm, Yantai Jiangyou silica gel thin-layer chromatography). Flash column chromatography was performed using Puke silica gel (ZCX-II, 200-300 mesh). NMR spectra were recorded on a Bruker ADVANCE 400 ($^1$H: 400 MHz; $^{13}$C: 100 MHz) or Bruker ADVANCE 500 ($^1$H: 500 MHz; $^{13}$C: 125 MHz) nuclear magnetic resonance instrument. TMS was used as the internal standard, and the peak shape was described as s (singlet), d (doublet), t (triplet) and m (multiplet). High-resolution mass spectrometry (HRMS) was conducted using an ABI Q-star Elite high-resolution mass spectrometer; the purity of the final product was detected by a high-performance liquid (HPLC) Agilent 1260 series chromatograph (Agilent PN959990-902 Eclipse Plus C18 (250 mm*4.6 mm) chromatographic column), and the detection was measured at 254 nm.

Preparation of Compound 5

Synthesis of 3-(5-(4-acryloylpiperazin-1-yl)-2-(trifluoromethyl)phenyl)-4-(1H-indol-3-yl)-1H-pyrrole-2,5-dione (Compound 5)

Step 1:
2-(5-fluoro-2-(trifluoromethyl)phenyl)acetamide (Compound 38a)

CDI (1.0 g, 4.5 mmol) was added to a solution of (5-fluoro-2-(trifluoromethyl)phenyl)acetic acid in 4 mL of DMF in batches. After stirring for 0.5 h at room temperature (rt), NH$_3$ (3.6 mL, 7 N in methanol solution) was added dropwise, and allowed to stir for another 1 hour at rt. The solvent was evaporated, water and ethyl acetate (2×120 mL) were used to extract the product. The organic phase was washed with saturated brine (2×40 mL), collected, dried over anhydrous Na$_2$SO$_4$, concentrated, and then separated and purified by column chromatography to give a white solid (0.73 g) with a yield of 73%.

$^1$HNMR (400 MHz, DMSO-d$_6$) δ 7.75 (dd, J=8.7, 5.6 Hz, 1H), 7.52 (s, 1H), 7.32 (m, 2H), 7.03 (s, 1H), 3.66 (s, 2H); MS (ESI) m/z 222.0 (M+H)$^+$.

Step 2: 3-(5-fluoro-2-(trifluoromethyl)phenyl)-4-(1H-indol-3-yl)-1H-pyrrole-2,5-dione (Compound 40a)

At 0° C., $^t$BuOK (5.5 mL, 1 M in THF) was added to a solution of Compound 38a (0.30 g, 1.3 mmol) and Compound 39 (0.41 g, 2.0 mmol) in anhydrous THF (8.0 mL). The solution was stirred for 45 min at 10° C. After the completion of the reaction (detected by TLC), HCl (5N) was added to adjust pH to 6, the solvent was removed, the mixture was extracted with ethyl acetate (2×120 mL), and the organic phase was washed with saturated brine (2×40 mL), collected, dried over anhydrous Na$_2$SO$_4$, concentrated, and then separated and purified by column chromatography to give a yellow solid (0.35 g) with a yield of 66%.

$^1$HNMR (400 MHz, DMSO-d$_6$) δ 11.99 (s, 1H), 11.23 (s, 1H), 8.02 (d, J=3.0 Hz, 1H), 7.97 (dd, J=8.9, 5.4 Hz, 1H), 7.60-7.52 (m, 1H), 7.49-7.38 (m, 2H), 7.07 (ddd, J=8.1, 7.0, 1.1 Hz, 1H), 6.75 (ddd, J=8.2, 7.1, 1.1 Hz, 1H), 6.46 (d, J=8.3 Hz, 1H).

$^{13}$CNMR (101 MHz, DMSO) δ 172.48, 172.01, 165.30, 162.80, 137.08, 136.25, 132.67, 126.18, 125.48, 125.25, 122.91, 120.95, 120.56, 120.19, 119.96, 117.31, 117.09, 112.94, 105.14.

MS (ESI) m/z 375.1 (M+H)$^+$.

Step 3: Tert-butyl 4-(3-(4-(1H-indol-3-yl)-2,5-di-oxo-2,5-dihydro-1H-pyrrol-3-yl)-4-(trifluoromethyl)phenyl)piperazine-1-carboxylate (Compound 41a)

1-Boc-piperazine (0.44 g, 2.4 mmol) was added to a solution of Compound 40a (0.3 g, 0.55 mmol) in DMSO (2.0 mL) and the mixture was refluxed overnight at 150° C. After the completion of the reaction (detected by TLC), the mixture was cooled down to rt, extracted with ethyl acetate (2×120 mL), and the organic phase was washed with saturated brine (2×40 mL), collected, dried over anhydrous $Na_2SO_4$, concentrated, and then separated and purified by column chromatography to give a yellow solid (0.35 g) with a yield of 66%.

$^1$HNMR (400 MHz, DMSO-$d_6$) δ 11.88 (s, 1H), 11.10 (s, 1H), 7.95 (d, J=2.9 Hz, 1H), 7.64 (d, J=9.0 Hz, 1H), 7.38 (d, J=8.1 Hz, 1H), 7.18-7.10 (m, 1H), 7.09-6.99 (m, 1H), 6.92 (d, J=2.6 Hz, 1H), 6.72 (dd, J=8.2, 7.0 Hz, 1H), 6.61 (d, J=8.2 Hz, 1H), 3.34-3.22 (m, 5H), 3.24-3.09 (m, 4H), 1.38 (s, 9H).

$^{13}$CNMR (101 MHz, DMSO) δ 172.85, 172.40, 154.34, 152.82, 136.97, 135.64, 132.09, 131.86, 131.85, 128.70, 128.42, 126.50, 126.50, 125.39, 125.38, 122.69, 121.37, 120.70, 117.97, 114.87, 112.64, 105.55, 79.57, 49.00, 47.32, 30.63, 29.52, 28.55.

MS (ESI) m/z 541.2 (M+H)$^+$.

Step 4: 3-(5-(4-acryloylpiperazin-1-yl)-2-(trifluoromethyl)-phenyl)-4-(1H-indol-3-yl)-1H-pyrrole-2,5-dione (Compound 5)

Trifluoroacetyl acid (TFA) (2.0 mL) was added to a solution of Compound 41a (0.10 g, 0.18 mmol) in DCM (2.0 mL) and the mixture was stirred at rt for 15 min. After the completion of the reaction (detected by TLC), TFA and DCM were evaporated, and the residue was dried and used in the next step without further purification. The residue was dissolved in a mixture of THF (2.0 mL) and water (1 drop), followed by adding DIEA (0.10 mL, 0.36 mmol) and acryloyl chloride (24 μL, 0.27 mmol). The ice bath was removed and the resulting solution was stirred at rt for 10 min. After the completion of the reaction (detected by TLC), the mixture was extracted with ethyl acetate (2×120 mL), and the organic phase was washed with saturated brine (2×40 mL), collected, dried over anhydrous $Na_2SO_4$, concentrated, and then separated and purified by column chromatography to give a yellow solid (73 mg) with a yield of 82%.

$^1$HNMR (400 MHz, DMSO-$d_6$) δ 11.88 (d, J=3.0 Hz, 1H), 11.11 (s, 1H), 7.96 (d, J=2.6 Hz, 1H), 7.65 (d, J=8.9 Hz, 1H), 7.38 (d, J=8.1 Hz, 1H), 7.18-7.10 (m, 1H), 7.08-7.00 (m, 1H), 6.96 (d, J=2.5 Hz, 1H), 6.76 (m, 2H), 6.65 (d, J=8.3 Hz, 1H), 6.11 (dd, J=16.6, 2.4 Hz, 1H), 5.68 (dd, J=10.4, 2.4 Hz, 1H), 3.66-3.46 (m, 4H), 3.23 (m, 4H).

$^{13}$CNMR (101 MHz, DMSO) δ 172.64, 172.20, 164.62, 152.49, 136.73, 135.43, 131.85, 131.65, 128.49, 128.34, 127.86, 126.28, 125.18, 123.57, 122.50, 121.15, 120.51, 117.67, 114.54, 112.42, 105.35, 47.58, 47.01, 44.37, 40.90.

HRMS (ESI) m/z calculated value for $C_{26}H_{21}F_3N_4O_3$ [M+H]$^+$: 495.1566; found, 495.1578.

Preparation of Compound 20

Synthesis of 3-(5-(4-acryloylpiperazin-1-yl)-2-(trifluoromethyl)phenyl)-4-(6-fluoro-1H-indol-3-yl)-1H-pyrrole-2,5-dione (Compound 20)

Step 1: Ethyl 2-(6-fluoro-1H-indol-3-yl)-2-oxoacetate (Compound 43a)

To a solution of Compound 42a (0.50 g, 3.7 mmol) in DCM (40 mL) was added 5.6 mL of $Et_2AlCl$ (1 M in hexane) under ice bath. The mixture was stirred at 0° C. for 30 min. To this solution was added ethyl oxalyl monochloride (0.61 mL, 5.5 mmol) as dropwise at 0° C. The resulting solution was stirred at 0° C. for 2 h, then ice water was added to quench the reaction after the reaction was completed (detected by TLC). The solvent was evaporated, water and ethyl acetate (3×50 mL) were used to extract the product. The organic phase was washed with saturated brine (2×30 mL), collected, dried over anhydrous $Na_2SO_4$, concentrated, and then separated and purified by column chromatography to give a grayish white solid (0.38 g) with a yield of 50%.

$^1$HNMR (400 MHz, DMSO-$d_6$) δ 12.41 (s, 1H), 8.44 (s, 1H), 8.14 (dd, J=8.7, 5.5 Hz, 1H), 7.35 (dd, J=9.5, 2.4 Hz, 1H), 7.13 (ddd, J=9.8, 8.7, 2.4 Hz, 1H), 4.35 (q, J=7.1 Hz, 2H), 1.33 (t, J=7.1 Hz, 3H).

MS (ESI) m/z 236.1 (M+H)$^+$.

Step 2: 3-(6-fluoro-1H-indol-3-yl)-4-(5-fluoro-2-(trifluoromethyl)phenyl)-1H-pyrrole-2,5-dione (Compound 44a)

At 0° C., $^t$BuOK (4.0 mL, 1 M in THF) was added to a solution of Compound 38a (0.19 g, 0.85 mmol) and Compound 43a (0.30 g, 1.3 mmol) in anhydrous THF (4.0 mL). The solution was stirred for 1 h at 10° C. After the completion of the reaction (detected by TLC), HCl (5N) was added to adjust pH to 6, the solvent was removed, the mixture was extracted with ethyl acetate (3×50 mL), and the organic phase was washed with saturated brine (2×20 mL), collected, dried over anhydrous $Na_2SO_4$, concentrated, and then separated and purified by column chromatography to give a yellow solid (0.25 g) with a yield of 75%.

$^1$HNMR (400 MHz, DMSO-$d_6$) δ 12.06 (s, 1H), 11.26 (s, 1H), 8.03 (d, J=3.1 Hz, 1H), 8.00 (dd, J=8.9, 5.4 Hz, 1H), 7.60 (m, 1H), 7.49 (dd, J=9.2, 2.7 Hz, 1H), 7.42 (dd, J=8.9, 4.8 Hz, 1H), 6.94 (m, 1H), 6.14 (dd, J=11.1, 2.5 Hz, 1H).

MS (ESI) m/z 393.0 (M+H)$^+$.

Step 3: tert-butyl 4-(3-(4-(6-fluoro-1H-indol-3-yl)-2,5-dioxo-2,5-dihydro-1H-pyrrol-3-yl)-4-(trifluoromethyl)phenyl)piperazine-1-carboxylate (Compound 45a)

1-Boc-piperazine (0.44 g, 2.4 mmol) was added to a solution of Compound 44a (0.3 g, 0.55 mmol) in DMSO (2.0 mL) and the mixture was refluxed overnight at 150° C. After the completion of the reaction (detected by TLC), the mixture was cooled down to rt, extracted with ethyl acetate (2×120 mL), and the organic phase was washed with saturated brine (2×40 mL), collected, dried over anhydrous $Na_2SO_4$, concentrated, and then separated and purified by column chromatography to give a yellow solid (0.35 g) with a yield of 30%.

$^1$HNMR (400 MHz, DMSO-$d_6$) δ 11.87 (s, 1H), 11.13 (s, 1H), 7.89 (s, 1H), 7.64 (d, J=9.0 Hz, 1H), 7.17 (dd, J=9.5, 2.3 Hz, 1H), 7.13 (dd, J=8.8, 2.6 Hz, 1H), 6.94 (d, J=2.6 Hz, 1H), 6.70-6.57 (m, 2H), 3.33-3.25 (m, 4H), 3.22 (m, 4H), 1.39 (s, 9H).
MS (ESI) m/z 559.2 (M+H)$^+$.

Step 4: 3-(5-(4-acryloylpiperazin-1-yl)-2-(trifluoromethyl)-phenyl)-4-(6-fluoro-1H-indol-3-yl)-1H-pyrrole-2,5-dione (Compound 20)

Trifluoroacetyl acid (TFA) (2.0 mL) was added to a solution of Compound 45a (0.10 g, 0.18 mmol) in DCM (2.0 mL) and the mixture was stirred at rt for 15 min. After the completion of the reaction (detected by TLC), TFA and DCM were evaporated, and the residue was dried and used in the next step without further purification. The residue was dissolved in a mixture of THF (2.0 mL) and water (1 drop), followed by adding DIEA (0.10 mL, 0.36 mmol) and acryloyl chloride (24 μL, 0.27 mmol). The ice bath was removed and the resulting solution was stirred at rt for 10 min. After the completion of the reaction (detected by TLC), the mixture was extracted with ethyl acetate (2×120 mL), and the organic phase was washed with saturated brine (2×40 mL), collected, dried over anhydrous Na$_2$SO$_4$, concentrated, and then separated and purified by column chromatography to give a yellow solid (73 mg) with a yield of 80%.
$^1$HNMR (400 MHz, DMSO-d$_6$) δ 11.86 (s, 1H), 11.12 (s, 1H), 7.87 (s, 1H), 7.64 (d, J=9.0 Hz, 1H), 7.21-7.08 (m, 2H), 6.97 (d, J=2.3 Hz, 1H), 6.78 (m, 1H), 6.69 (m, 1H), 6.62 (m, 1H), 6.11 (dd, J=16.7, 2.3 Hz, 1H), 5.68 (dd, J=10.4, 2.3 Hz, 1H), 3.55 (m, 4H), 3.24 (m, 4H).
$^{13}$CNMR (101 MHz, DMSO-d$_6$) δ 172.70, 172.30, 164.88, 158.20, 152.82, 137.14, 137.02, 135.41, 132.57, 129.48, 128.63, 128.05, 122.60, 122.51, 122.17, 117.72, 114.79, 109.16, 108.92, 105.65, 98.84, 98.59, 47.75, 47.16, 44.65, 41.14.
HRMS (ESI) m/z calculated value for C$_{26}$H$_{20}$F$_4$N$_4$O$_3$ [M+H]$^+$: 513.1472; found, 513.1479. Purity: 99.2%.

Preparation of Compound 28

Synthesis of 3-(5-(4-acryloylpiperazin-1-yl)-2-methoxyphenyl)-4-(1H-indol-3-yl)-1H-pyrrole-2,5-dione (Compound 28)

Step 1: 2-(5-(4-(tert-butoxycarbonyl)piperazin-1-yl)-2-methoxyphenyl)acetic Acid (Compound 47d)

Compound 46d (0.52 g, 2.0 mmol), 1-Boc-piperazine (0.49 g, 2.6 mmol), sodium tert-butoxide (0.59 g, 2.6 mmol), 2-(ditert-butylphosphino)biphenyl (JohnPhos, 0.16 g, 0.41 mmol), and Pd$_2$(dba)$_3$ (0.19 g, 0.20 mmol) were taken up in anhydrous PhMe (15 mL) in a microwave vial and purged with argon gas to remove oxygen. The vial was capped and heat to 110° C. for 1 h. After cooling to rt and the reaction was completed (detected by TLC), the mixture was filtered through diatomite, and the filtrate was adjusted to a pH of 5 and extracted with ethyl acetate (3×100 mL). The organic phase was washed with saturated brine (2×40 mL), collected, dried over anhydrous Na$_2$SO$_4$, concentrated, and then separated and purified by column chromatography to give a white solid (0.35 g) with a yield of 49%.
$^1$HNMR (500 MHz, DMSO-d$_6$) δ 6.87-6.84 (m, 1H), 6.84 (s, 1H), 6.82 (d, J=2.8 Hz, 1H), 3.68 (s, 3H), 3.45 (s, 2H), 3.45-3.41 (m, 4H), 2.95-2.93 (m, 4H), 1.42 (s, 9H).
$^{13}$CNMR (126 MHz, DMSO) δ 173.04, 154.32, 152.01, 145.32, 124.49, 121.12, 116.45, 111.74, 79.40, 56.13, 50.34, 36.23, 28.53.
MS/ESI 351.2 (M+1)$^+$.

Step 2: tert-butyl 4-(3-(2-amino-2-oxoethyl)-4-methoxyphenyl)piperazine-1-carboxylate (Compound 48d)

CDI (0.29 g, 1.29 mmol) was added in batches to a solution of Compound 47d (0.30 g, 0.86 mmol) in 4.0 mL of DMF. After stirring for 0.5 h at rt, NH$_3$ (0.6 mL, 7 N in methanol solution) was added and allowed to stir for another 1 h at rt. The solvent was evaporated, water and ethyl acetate (2×120 mL) were used to extract the product. The organic phase was washed with saturated brine (2×40 mL), collected, dried over anhydrous Na$_2$SO$_4$, concentrated, and then separated and purified by column chromatography to give a white solid (0.73 g) with a yield of 73%.
$^1$HNMR (400 MHz, DMSO-d$_6$) δ 7.75 (dd, J=8.7, 5.6 Hz, 1H), 7.52 (s, 1H), 7.32 (m, 2H), 7.03 (s, 1H), 3.66 (s, 2H);
MS (ESI) m/z 222.0 (M+H)$^+$.

Step 3: tert-butyl 4-(3-(4-(1H-indol-3-yl)-2,5-dioxo-2,5-dihydro-1H-pyrrol-3-yl)-4-methoxyphenyl)piperazine-1-carboxylate (Compound 49d)

At 0° C., $^t$BuOK (2.2 mL, 1 M in THF) was slowly added to a solution of Compound 48d (0.2 g, 0.57 mmol) and Compound 38a (0.17 g, 0.85 mmol) in anhydrous THF (4.0 mL). The solution was stirred for 1 h at 10° C. After the completion of the reaction (detected by TLC), HCl (5N) was added to adjust pH to 5, the solvent was removed, the mixture was extracted with ethyl acetate (3×40 mL), and the organic phase was washed with saturated brine (2×20 mL), collected, dried over anhydrous Na$_2$SO$_4$, concentrated to give an intermediate Compound 49d.
MS (ESI) m/z 503.2 (M+H)$^+$.

Step 4: 3-(1H-indol-3-yl)-4-(2-methoxy-5-(piperazin-1-yl)phenyl)-1H-pyrrole-2,5-dione (Compound 50d)

Trifluoroacetyl acid (TFA) (2.0 mL) was added to a solution of Compound 49d (0.12 g, 0.24 mmol) in DCM (2.0 mL) and the mixture was stirred at rt for 15 min. After the completion of the reaction (detected by TLC), TFA and DCM were evaporated, and the mixture was extracted with water and ethyl acetate (2×60 mL), and the organic phase was washed with saturated brine (2×30 mL), collected, dried over anhydrous Na$_2$SO$_4$, concentrated, and then separated and purified by column chromatography to give a yellow solid (0.15 g) with a yield of 52%.
$^1$HNMR (400 MHz, DMSO-d$_6$) δ 11.80 (s, 1H), 7.91 (s, 1H), 7.37 (d, J=8.1 Hz, 1H), 7.02 (ddd, J=8.2, 7.0, 1.1 Hz, 1H), 6.95 (dd, J=9.0, 3.0 Hz, 1H), 6.88 (d, J=9.1 Hz, 1H), 6.78 (d, J=2.9 Hz, 1H), 6.65 (ddd, J=8.2, 7.0, 1.1 Hz, 1H), 6.51-6.41 (m, 1H), 3.26 (s, 3H), 2.89-2.81 (m, 4H), 2.80-2.78 (m, 4H).
$^{13}$CNMR (101 MHz, DMSO) δ 173.08, 172.67, 152.06, 145.93, 136.87, 134.69, 130.87, 128.29, 125.38, 122.39, 121.29, 121.12, 120.23, 119.96, 118.58, 113.08, 112.38, 106.29, 55.97, 50.91, 45.78.
MS/ESI 503.2 (M+1)$^+$.

Step 5: 3-(5-(4-acryloylpiperazin-1-yl)-2-methoxyphenyl)-4-(1H-indol-3-yl)-1H-pyrrole-2,5-dione (Compound 28)

Compound 50d (0.12 g, 0.24 mmol) was dissolved in a mixture of THF (2.0 mL) and water (1 drop), followed by adding DIEA (0.16 mL, 0.96 mmol) and acryloyl chloride (30 μL, 0.36 mmol). The ice bath was removed, and the resulting solution was stirred at rt for 10 min. After completion of the reaction (detected by TLC), the mixture was extracted with ethyl acetate (2×60 mL). The organic phase was washed with saturated brine (2×30 mL), collected, dried over anhydrous $Na_2SO_4$, concentrated, and then separated and purified by column chromatography to give a yellow solid (90 mg) with a yield of 82%.

$^1$HNMR (400 MHz, DMSO-$d_6$) δ 11.81 (s, 1H), 10.93 (s, 1H), 7.93 (d, J=2.8 Hz, 1H), 7.38 (d, J=8.1 Hz, 1H), 7.07-6.98 (m, 2H), 6.92 (d, J=9.0 Hz, 1H), 6.84 (d, J=2.9 Hz, 1H), 6.80 (dd, J=16.7, 10.5 Hz, 1H), 6.66 (t, J=7.3 Hz, 1H), 6.45 (d, J=8.1 Hz, 1H), 6.10 (dd, J=16.7, 2.4 Hz, 1H), 5.68 (dd, J=10.4, 2.4 Hz, 1H), 3.59 (m, 4H), 3.29 (s, 3H), 2.91 (m, 4H).

$^{13}$CNMR (101 MHz, DMSO-$d_6$) δ 173.05, 172.62, 164.74, 152.47, 144.97, 136.88, 134.75, 130.96, 128.69, 128.10, 127.93, 125.33, 122.42, 121.25, 121.20, 120.60, 120.26, 119.13, 113.12, 112.42, 106.23, 55.98, 50.83, 50.22, 45.27, 41.73.

HRMS (ESI) m/z calculated value for $C_{26}H_{24}N_4O_4$ [M+H]$^+$: 457.1798; found, 457.1794.

Preparation of Compound 32

Step 1: 2-(5-fluoro-2-(nitro)phenyl)acetamide (Compound 38b)

CDI (1.2 g, 7.5 mmol) was added in batches to a solution of 5-fluoro-2-(nitro)phenylacetic acid (1.0 g, 5.0 mmol) in 4.0 mL of DMF. After stirring for 0.5 h at rt, $NH_3$ (3.5 mL, 7 N in methanol solution) was added as dropwise and allowed to stir for another 1 h at rt. The solvent was evaporated, water and ethyl acetate (2×120 mL) were used to extract the product. The organic phase was washed with saturated brine (2×40 mL), collected, dried over anhydrous $Na_2SO_4$, concentrated, and then separated and purified by column chromatography to give a white solid (0.70 g) with a yield of 70%.

$^1$H NMR (400 MHz, DMSO-$d_6$) δ 8.11 (dd, J=9.0, 5.2 Hz, 1H), 7.54 (s, 1H), 7.46-7.29 (m, 2H), 7.02 (s, 1H), 3.88 (s, 2H).

MS (ESI) m/z 199.1 (M+H)$^+$.

Step 2: 3-(5-fluoro-2-(nitro)phenyl)-4-(1H-indol-3-yl)-1H-pyrrole-2,5-dione (Compound 40b)

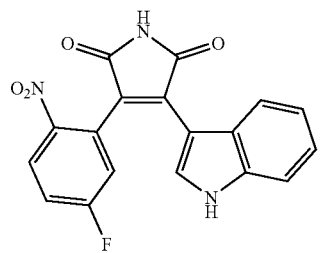 [SMILES: O=C1NC(=O)C(c2c[nH]c3ccccc23)=C1c1cc(F)ccc1[N+](=O)[O-]]

At 0° C., $^t$BuOK (7.5 mL, 1 M in THF) was slowly added to a solution of Compound 38b (0.30 g, 1.5 mmol) and Compound 39 (0.45 g, 2.2 mmol) in anhydrous THF (15 mL). The solution was stirred for 45 min at 10° C. After the completion of the reaction (detected by TLC), HCl (5N) was added to adjust pH to 6, the solvent was removed, the mixture was extracted with ethyl acetate (2×120 mL), and the organic phase was washed with saturated brine (2×40 mL), collected, dried over anhydrous $Na_2SO_4$, concentrated to give a yellow solid 0.30 g with a yield of 72%.

MS (ESI) m/z 352.2 (M+H)$^+$.

Step 3: Tert-butyl 4-(3-(4-(1H-indol-3-yl)-2,5-dioxo-2,5-dihydro-1H-pyrrol-3-yl)-4-(nitro)phenyl)piperazine-1-carboxylate (Compound 41b)

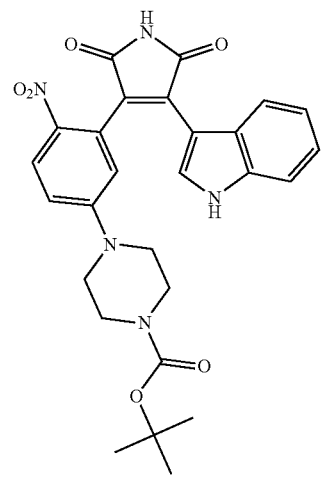 [SMILES: CC(C)(C)OC(=O)N1CCN(c2ccc([N+](=O)[O-])c(C3=C(c4c[nH]c5ccccc45)C(=O)NC3=O)c2)CC1]

1-Boc-piperazine (0.64 g, 3.4 mmol) was added to a solution of Compound 40b (0.3 g, 0.85 mmol) in DMSO (2.0 mL) and the mixture was refluxed overnight at 150° C. After the completion of the reaction (detected by TLC), the mixture was cooled down to rt, extracted with ethyl acetate (2×120 mL), and the organic phase was washed with saturated brine (2×40 mL), collected, dried over anhydrous $Na_2SO_4$, concentrated, and then separated and purified by column chromatography to give a yellow solid (0.27 g) with a yield of 62%.

$^1$H NMR (400 MHz, DMSO-$d_6$) δ 11.94 (s, 1H), 11.12 (s, 1H), 8.17 (d, J=9.4 Hz, 1H), 8.03 (s, 1H), 7.42 (d, J=8.1 Hz, 1H), 7.16-6.94 (m, 2H), 6.74 (t, J=7.6 Hz, 1H), 6.65-6.49 (m, 2H), 3.14 (d, J=48.7 Hz, 4H), 2.97 (s, 4H), 1.37 (s, 9H).

$^{13}$C NMR (101 MHz, DMSO) δ 172.88, 171.47, 154.25, 153.43, 137.86, 137.08, 132.84, 131.86, 129.73, 129.47, 127.83, 124.65, 122.61, 121.04, 120.56, 116.08, 114.18, 112.80, 104.45, 79.61, 60.29, 57.90, 46.77, 28.52.

MS (ESI) m/z 518.4 (M+H)$^+$.

Step 4: 3-(5-(4-acryloylpiperazin-1-yl)-2-(nitro) phenyl)-4-(1H-indol-3-yl)-1H-pyrrole-2,5-dione (Compound 32)

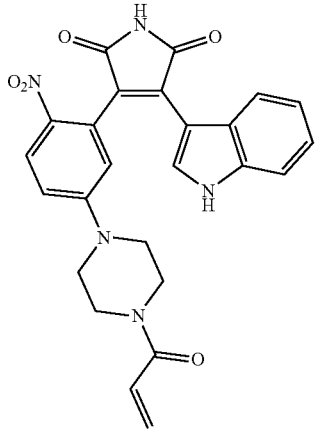 [SMILES: C=CC(=O)N1CCN(c2ccc([N+](=O)[O-])c(C3=C(c4c[nH]c5ccccc45)C(=O)NC3=O)c2)CC1]

Trifluoroacetyl acid (TFA) (2.0 mL) was added to a solution of Compound 41b (0.10 g, 0.19 mmol) in DCM (2.0 mL) and the mixture was stirred at rt for 15 min. After the completion of the reaction (detected by TLC), TFA and DCM were evaporated, and the residue was dried and used in the next step without further purification. The residue was dissolved in a mixture of THF (2.0 mL) and water (1 drop), followed by adding DIEA (70 μL, 0.38 mmol) and acryloyl chloride (26 μL, 0.28 mmol). The ice bath was removed and the resulting solution was stirred at rt for 10 min. After the completion of the reaction (detected by TLC), the mixture was extracted with ethyl acetate (2×120 mL), and the organic phase was washed with saturated brine (2×40 mL), collected, dried over anhydrous $Na_2SO_4$, concentrated, and then separated and purified by column chromatography to give a yellow solid (70 mg) with a yield of 78%.

$^1$H NMR (400 MHz, DMSO-$d_6$) δ 11.96 (s, 1H), 11.14 (s, 1H), 8.18 (d, J=9.3 Hz, 1H), 8.03 (s, 1H), 7.41 (d, J=8.1 Hz, 1H), 7.07 (d, J=9.6 Hz, 1H), 7.02 (d, J=7.9 Hz, 1H), 6.82-6.71 (m, 1H), 6.70-6.62 (m, 1H), 6.60-6.50 (m, 2H), 6.08 (d, J=16.6 Hz, 1H), 5.66 (d, J=10.5 Hz, 1H), 3.26 (m, 4H), 3.10 (m, 4H).

$^{13}$C NMR (101 MHz, DMSO-$d_6$) δ 173.17, 171.51, 164.85, 153.40, 138.29, 137.06, 133.13, 131.87, 129.76, 128.52, 128.09, 127.85, 124.69, 122.67, 121.05, 120.60, 115.95, 114.10, 112.83, 104.46, 80.45, 47.53, 46.29, 44.15, 43.52.

HRMS (ESI) m/z calculated value for $C_{25}H_{21}N_5O_5$ [M+H]$^+$: 472.1543; found, 472.1539.

Preparation of Compound 34

Synthesis of 3-(1-acryloylpiperidin-4-yl)amino)-4-(1H-indol-3-yl)-1H-pyrrole-2,5-dione (Compound 34)

Step 1: 3-bromo-4-(1H-indol-3-yl)-1H-pyrrole-2,5-dione (Compound 52)

In a two-necked flask equipped with a dropping funnel under argon, indole (0.3 g, 1.2 mmol) was dissolved in anhydrous THF (8.0 mL). A solution of ethyl magnesium bromide in $Et_2O$ (1.57 mL, 4.7 mmol) was added dropwise into the mixture, which was then heated to reflux for 2 h. After cooling to rt, a solution of 3,4-dibromo-1H-pyrrole-2,5-dione (Compound 51, 0.55 g, 4.7 mmol) in THF was added dropwise over about 1 h. Then, the reaction mixture was stirred at rt for 1 h. After the completion of reaction (detected by TLC), the mixture was then hydrolyzed to pH=9 with aqueous HCl solution. After adding saturated aqueous $NH_4Cl$ solution, the aqueous phase was extracted with ethyl acetate (2×60 mL). The organic phase was washed with saturated brine (2×30 mL), collected, dried over anhydrous $Na_2SO_4$, concentrated, and then separated and purified by column chromatography to give a yellow solid (0.28 g) with a yield of 82%.

$^1$HNMR (400 MHz, DMSO-$d_6$) δ 12.10 (s, 1H), 11.35 (s, 1H), 8.03 (d, J=2.9 Hz, 1H), 7.89 (dt, J=8.1, 1.0 Hz, 1H), 7.51 (dt, J=8.1, 1.0 Hz, 1H), 7.22 (ddd, J=8.1, 7.0, 1.2 Hz, 1H), 7.14 (ddd, J=8.1, 7.1, 1.2 Hz, 1H).

$^{13}$CNMR (101 MHz, DMSO) δ 170.75, 167.99, 138.54, 137.01, 131.54, 125.05, 122.95, 122.77, 120.92, 115.13, 112.84, 104.25.

MS/ESI 291.0 (M+1)$^+$.

Step 2: tert-butyl 4-((4-(1H-indol-3-yl)-2,5-dioxo-2, 5-dihydro-1H-pyrrol-3-yl)amino)piperidine-1-carboxylate (Compound 53)

Compound 52 (0.13 g, 0.45 mmol) and Boc protected piperidin-4-amine (0.18 g, 0.89 mmol) were dissolved in DMSO (1.5 mL), followed by the addition of DIEA (0.15 mL, 0.89 mmol). The mixture was heated at 126° C. overnight. After cooling to rt and the completion of reaction (detected by TLC), water and ethyl acetate were used to extract the mixture. The organic phase was washed with saturated brine (2×20 mL), collected, dried over anhydrous $Na_2SO_4$, concentrated, and then separated and purified by column chromatography to give a yellow solid (0.11 g) with a yield of 60%.

$^1$HNMR (400 MHz, DMSO-$d_6$) δ 11.21 (d, J=2.5 Hz, 1H), 10.34 (s, 1H), 7.40 (d, J=8.1 Hz, 1H), 7.37-7.27 (m, 2H), 7.14-7.06 (m, 1H), 7.04-6.95 (m, 1H), 6.86 (d, J=9.0 Hz, 1H), 3.67 (m, 2H), 3.43 (m, 1H), 1.97 (m, 2H), 1.47 (m, 2H), 1.31 (s, 9H), 1.26 (m, 2H). $^{13}$CNMR (101 MHz, DMSO).

$^{13}$CNMR (101 MHz, DMSO) δ 173.82, 169.57, 154.19, 143.23, 136.10, 128.71, 126.48, 121.70, 119.91, 119.37, 112.05, 104.59, 100.05, 93.48, 79.22, 50.31, 32.01, 28.52.

MS/ESI 410.1 (M+1)$^+$.

Step 3: 3-((1-acryloylpiperidin-4-yl)amino)-4-(1H-indol-3-yl)-1H-pyrrole-2,5-dione (Compound 34)

TFA (2.0 mL) was added to a solution of Compound 53 (0.10 g, 0.18 mmol) in DCM (2.0 mL) and the mixture was stirred at rt for 15 min. After the completion of the reaction (detected by TLC), TFA and DCM were evaporated, and the residue was dried and used in the next step without further purification. The residue was dissolved in a mixture of THF (2.0 mL) and water (1 drop), followed by the addition of DIEA (0.10 mL, 0.36 mmol) and acryloyl chloride (24 μL, 0.27 mmol). The ice bath was removed and the resulting solution was stirred at rt for 10 min. After the completion of the reaction (detected by TLC), the mixture was extracted with ethyl acetate (2×120 mL), and the organic phase was washed with saturated brine (2×40 mL), collected, dried over anhydrous $Na_2SO_4$, concentrated, and then separated and purified by column chromatography to give a yellow solid (80 mg) with a yield of 90%.

¹HNMR (400 MHz, DMSO-d$_6$) δ 11.23 (s, 1H), 10.43 (s, 1H), 7.54-7.20 (m, 3H), 7.09 (d, J=7.1 Hz, 1H), 7.01 (t, J=7.0 Hz, 1H), 6.64 (d, J=7.5 Hz, 1H), 5.75 (t, J=14.6 Hz, 1H), 5.27 (d, J=7.8 Hz, 1H), 3.87 (d, J=12.2 Hz, 1H), 2.93 (m, 1H), 2.82 (m, 1H), 2.56 (m, 1H), 1.75 (m, 1H), 1.57 (m, 2H), 0.84 (m, 1H).

¹³CNMR (101 MHz, DMSO) δ 173.79, 169.60, 164.78, 142.34, 136.13, 128.48, 128.46, 127.84, 127.35, 126.68, 121.84, 119.96, 119.59, 112.24, 104.14, 50.10, 49.39, 41.81, 30.50, 28.52.

HRMS (ESI) m/z calculated value for $C_{20}H_{20}N_4O_3$[M+H]$^+$: 365.1535; found, 365.1541. Purity: 99.3%.

Biological Activity Test (1) Enzymatic Assay In Vitro

The enzymatic assay in vitro was performed with the conditions of K$_m$ ATP (0.6 micromole) and high-concentration ATP (1 millimole). The results of the enzymatic assay in vitro were listed in the table above.

The procedures for the enzymatic assay in vitro are as follows: Kinases were purchased from Carna Biosciences. The enzymatic activities of JAK3 were assessed using HTRF® KinEase™ assay with concentrations of ATP at Km and 1 mM, separately. The ATP Kinase enzymology assays were performed according to the protocols specified by HTRF® KinEase™ assay instructions (Cisbio Bioassays).

(2) Selectivity Assay

To evaluate the selectivity of Compound 32 against a panel of kinases, 50 representative kinases were selected for a preliminary selectivity assay, and the results are shown in FIG. 1.

Compound 32 was shown to have high selectivity. Tested at 1 µM against a panel of kinases, most kinases exhibited no more than 50% inhibition, and only three kinases PKCα, PKCγ and GSK3β exhibited more than 50% inhibition, which was consistent with the selectivity results of NIBR3049. Compound 32 also exhibited high selectivity within the JAK family and among other 10 kinases with a cysteine at a comparable position to Cys909, indicating that Compound 32, as a small molecule probe, can be used for the studies on JAK3 function and JAKs-STATs signal pathway.

(3) Cellular Activity Assay

To evaluate the cellular activities of Compound 32, the ability of Compound 32 to inhibit phosphorylation of a downstream substrate STAT5 in cells was detected.

Figure 2:
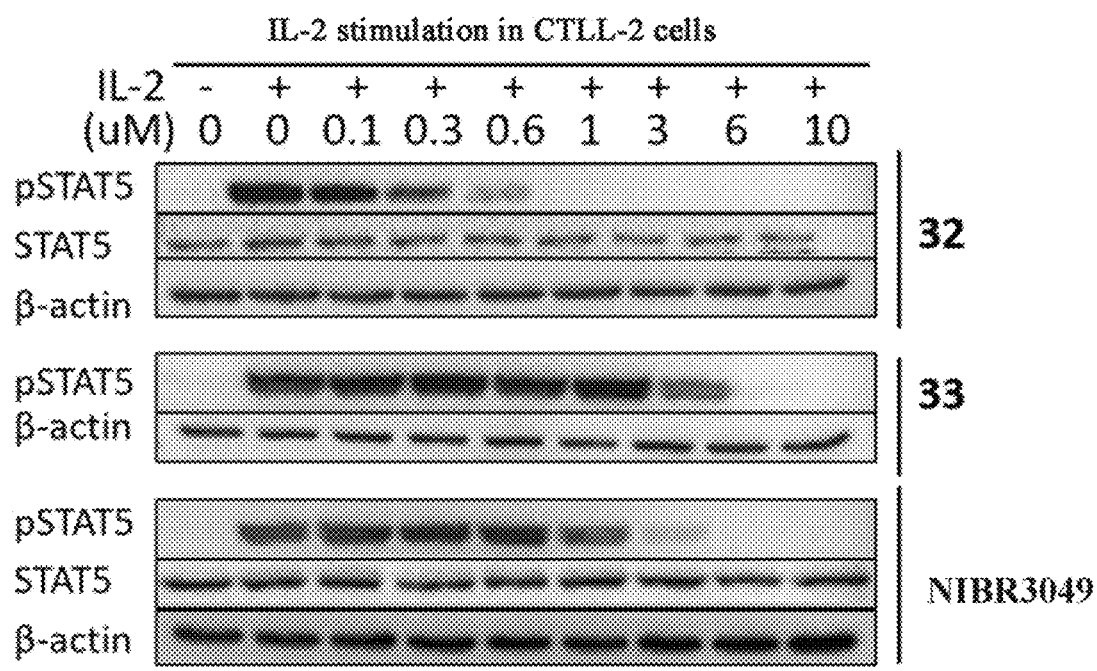
FIGS. 2-5: cellular activity assay results of compounds.
Figure 3:
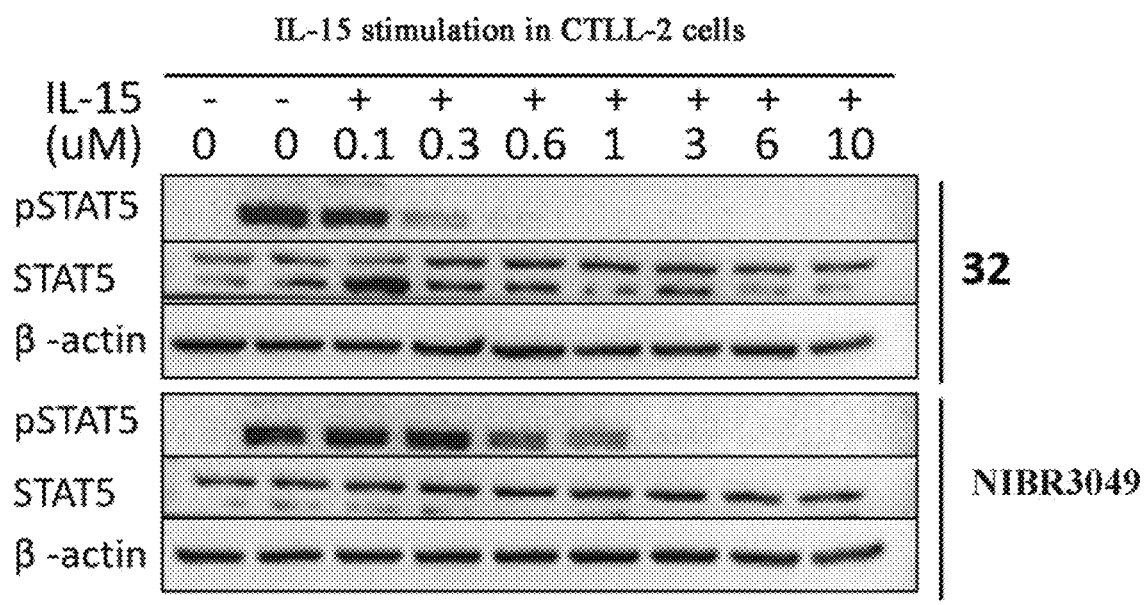

Mouse T cells (CTLL-2 cells) were deprived of growth factors and starved overnight. Then, cells were incubated with a specified concentration of a compound (JAK3 inhibitor or DMSO) at 37° C. for 2 hours. After stimulation with 500 ng/mL IL-2 or 500 ng/mL IL-5 (R&D Systems) for 30 min, cells were collected and lysed in cell lysis buffer containing protease and phosphatase inhibitors. Western blotting analyses were then conducted after separation by SDS/PAGE electrophoresis and transfer to nitrocellulose membranes. Phospho-STAT5, STAT5, and β-actin (all antibodies were from Cell Signaling Technologies) were blotted separately with specific antibodies. The results are shown in FIG. 2 and FIG. 3. The EC$_{50}$ values were calculated by quantitative stripe gray analysis using GraphPad Prism software.

In CTLL-2, IL-2-induced STAT5 phosphorylation was almost completely inhibited by 600 nanomoles of Compound 32 (EC$_{50}$=305 nanomoles). In comparison, 6000 nanomoles was required in Compound NIBR3049 treated cells to completely inhibit STAT5 activation (EC$_{50}$=1999 nanomoles). Compound 32 was more sensitive in inhibiting IL-15-induced STAT5 phosphorylation (EC$_{50}$=141 nanomoles).

Figure 4:
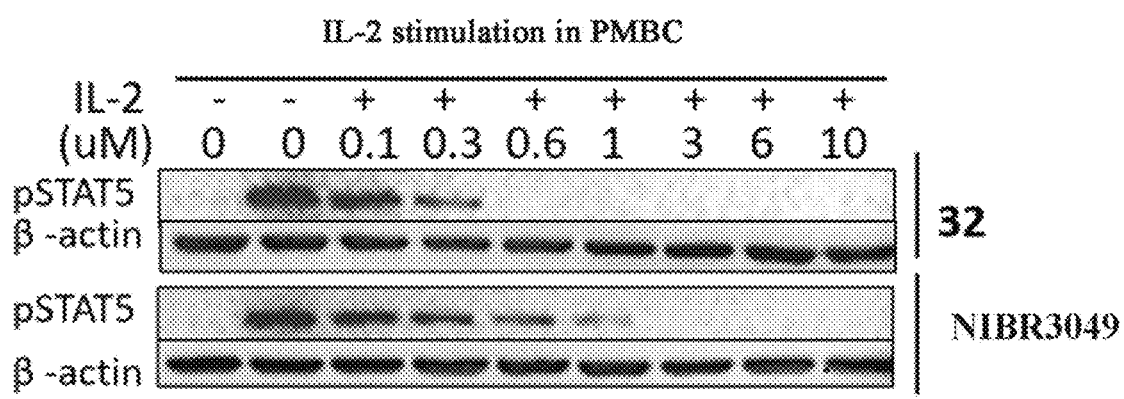
Figure 5:
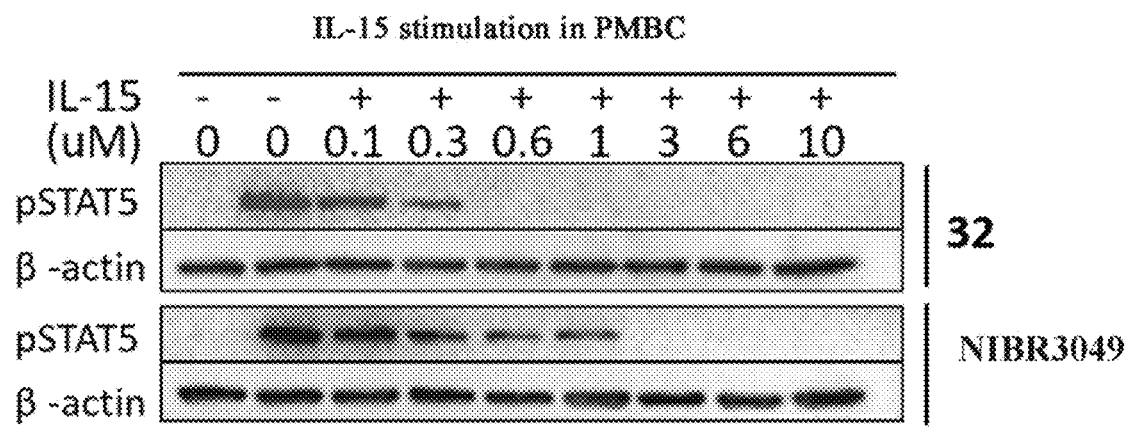

Similarly, in human peripheral blood mononuclear cells (PBMC), compared with NIBR3049, Compound 32 also exhibited higher inhibitory activity against IL-2 and IL-15-induced STAT5 phosphorylation. The results are shown in FIGS. 4 and 5.

Methods: After thawing, PBMCs (purchased from AllCells) were resuspended in RPMI-1640 containing 10% FBS overnight and then incubated with specified concentrations of JAK3 inhibitors or DMSO for 2 h. After stimulation with IL-2 (500 ng/mL, R&D Systems), IL-15 (500 ng/mL, R&D Systems), IL-6 (600 ng/mL, R&D Systems), or IFN-α (400 ng/mL, R&D Systems) for 30 min, cells were collected and lysed in cell lysis buffer containing protease and phosphatase inhibitors. Western blotting analyses were then conducted after separation by SDS/PAGE electrophoresis and transferred to nitrocellulose membranes. Phospho-STAT5, Phospho-STAT3, and phospho-STAT1 (all from Cell Signaling Technologies) were blotted separately with specific antibodies. β-actin was blotted for equal loading. The EC$_{50}$ values were calculated by quantitative stripe gray analysis using GraphPad Prism software.

(4) Cellular Selectivity Assay

Figure 6:
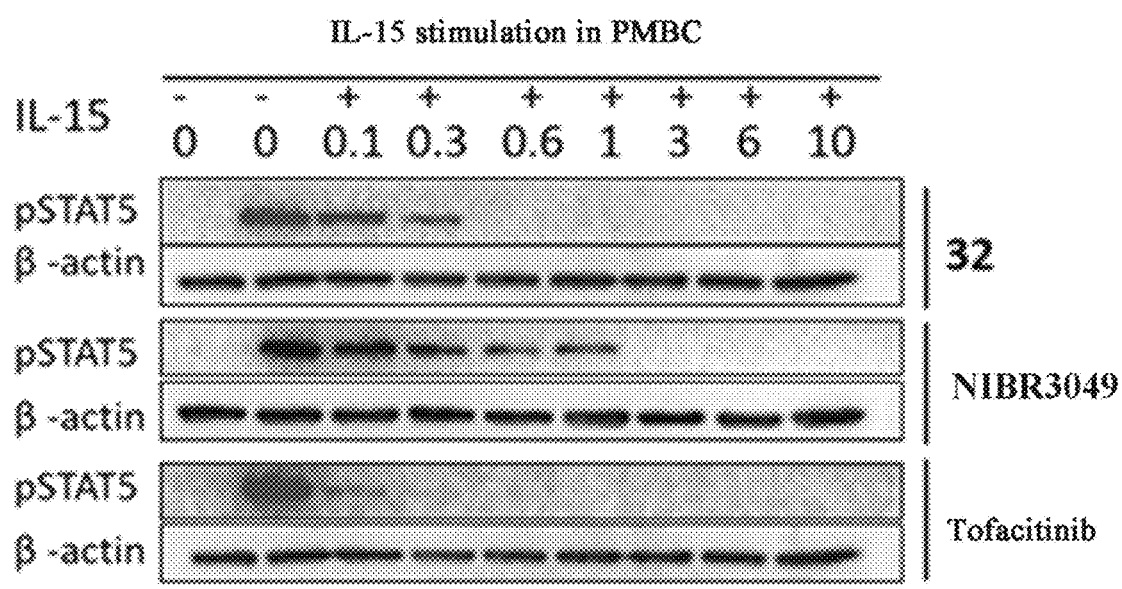
FIGS. 6-8: selectivity assay results of compounds in cells.
Figure 7:
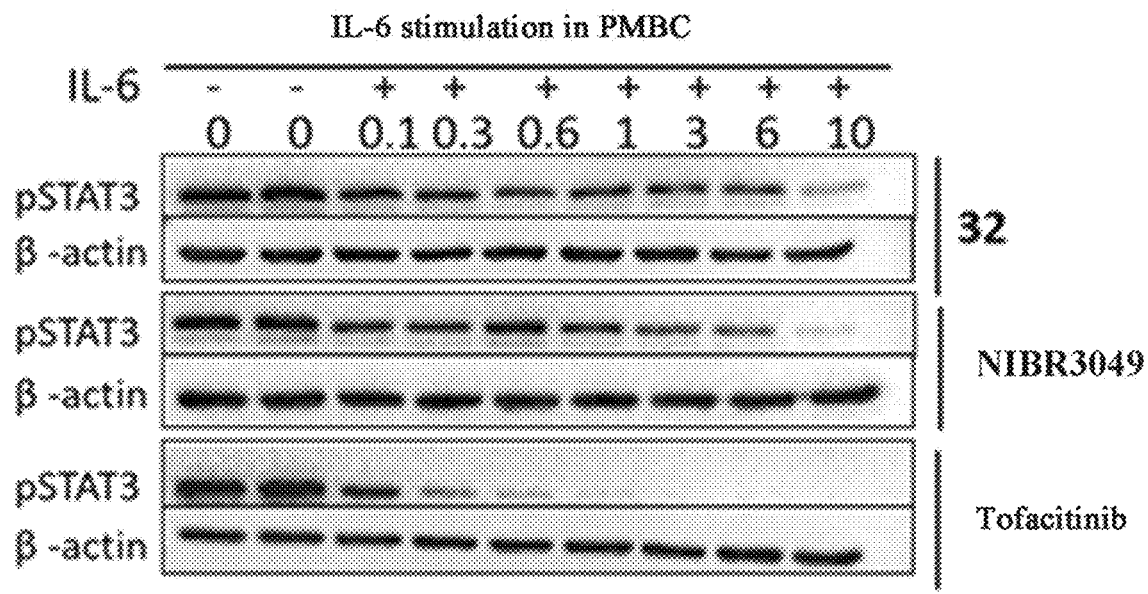
Figure 8:
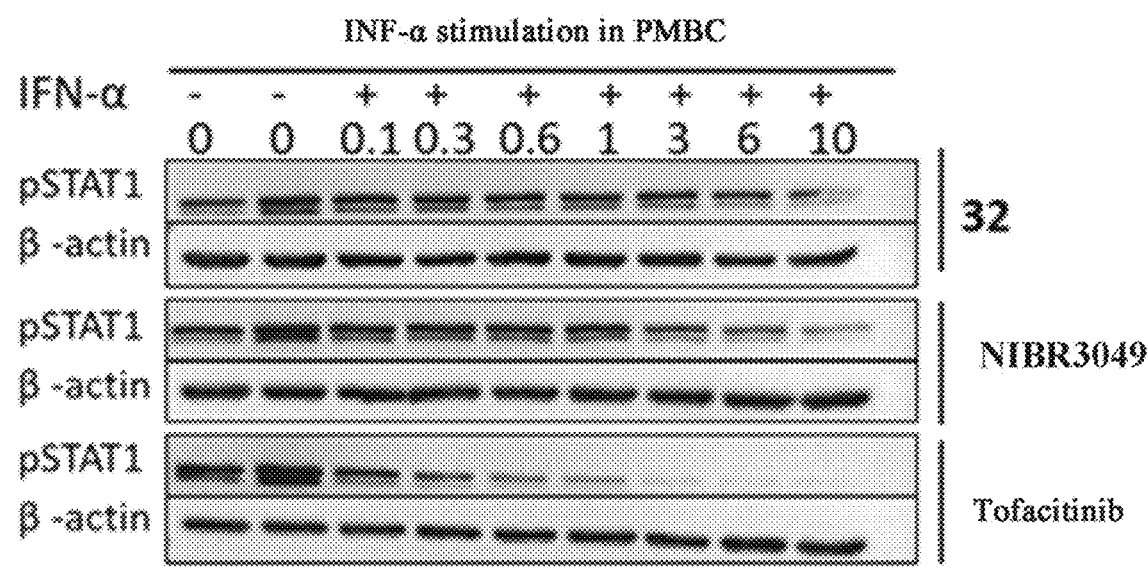

We further characterized the cellular selectivity of Compound 32 in PBMCs upon stimulation with different cytokines (IL-15, IL-6 or IFN-α) by detecting the inhibitory effects of compounds on the phosphorylation of downstream substrates of JAKs. The methods are as described in section (4), and the results are shown in FIGS. 6, 7 and 8.

Among these cytokines, only signaling via IL-15 is dependent on JAK3. Signaling via IL-6 is dependent on JAK1, JAK2 and TYK2, and signaling via IFN-α is exclusively related to JAK1 and TYK2. Compound 32 effectively abrogated phosphorylation of STAT5 at a concentration of 300 nM. In comparison, in 1-6 and IFN-α signal pathways, even at doses as high as 10 µM, only partial inhibition was observed for STAT3 phosphorylation and STAT1 phosphorylation. Compared with Compound NIBR3049, Compound 32 exhibited not only enhanced cellular activity, but also an improved selectivity for other JAKs in cellular environment with high-concentration ATP. In contrast, non-selective Tofacitinib did not show obvious selectivity in inhibiting the phosphorylation of downstream substrates stimulated by three cytokines.

(5) Cell Washout Experiment

In order to further prove that Compound 32 is covalently bound to JAK3 in cells, a cell washout experiment was performed.

Figure 9:
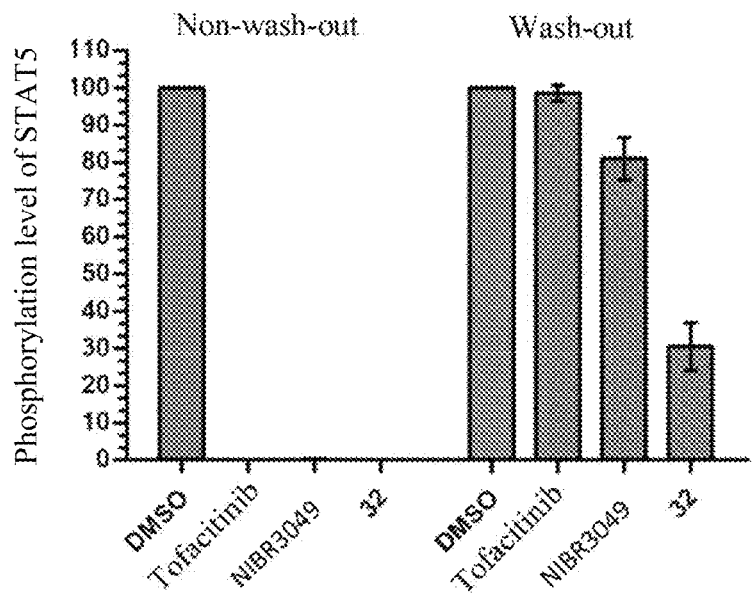
FIG. 9: evaluation results of compounds in a cell washout experiment.

The washout procedures are as follows: CTLL-2 cells were treated with compounds for 2 hours. Then, for washout groups, cells were washed three times with PBS. The non-washout groups were kept constant. Cells were then stimulated with IL-15 for 30 min, lysed, and subjected to standard Western blot. The results are shown in FIG. 9. Cells, treated with compounds, were extensively washed with PBS. Cells treated with Compound 32 (which is covalently bound to JAK3 in cells) sustained inhibition of STAT5 phosphorylation. In comparison, the inhibitory activities of the reversible inhibitor Tofacitinib and Compound NIBR3049 were almost lost after washing out. Because JAK1 does not have a cysteine at the same position as Cys909 in JAK3, Compound 32 would unlikely interfere JAK1 activity after washing out with PBS. Therefore, this washout experiment mitigated the influence of JAK1 and demonstrated that specific inhibition of JAK3 alone was sufficient to effectively inhibit IL-15-mediated $\gamma_c$ cytokine receptor signal pathway.

(6) Inhibition of LPS-Stimulated Inflammatory Cytokine Release

In rheumatoid arthritis (RA) patients, joint erosion is coincident with increases in inflammatory cytokines, including IL-6, IL-1β, TNF-α, and MCP-1. The release of IL-6, IL-1β, TNF-α and MCP-1 was regulated by the negative feedback of IL-10-JAKs-STAT3 signal pathway.

The LPS-induced IL-6 and TNF-α release assay was carried out as follows: frozen PBMCs (from Allcells) were thawed in RPMI1640 (Thermo Fisher) containing 10% FBS and recovered overnight at 37° C. The next day, cells were diluted to $1\times10^6$ cells/mL and seeded (500 μL) in 6-well plates. Compounds or DMSO (5 μL, serially diluted in DMSO) were added to the plates and incubated with cells for 2 h at 37° C., followed by stimulation with LPS (5 μL, 1 μg/mL) and incubation for 24 h at 37° C. in 5% $CO_2$. Supernatants were collected for determination of IL-6 and TNF-α levels using human IL-6 or human THF-α DuoSet ELISA Kits (R&D Systems) according to the manufacturer's instructions.

Figure 10:
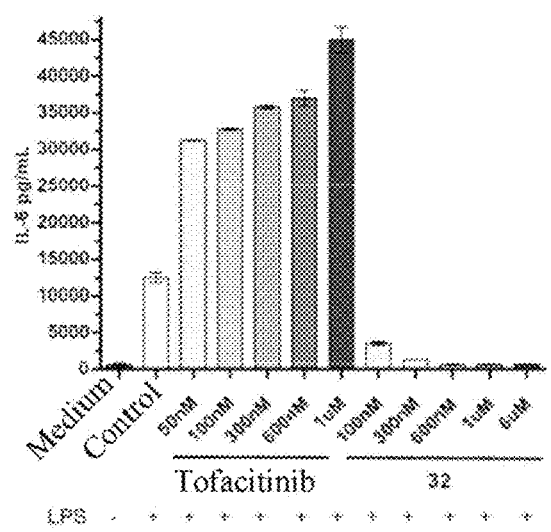
FIGS. 10-12: assay results of compounds in inhibiting release of stimulated inflammatory cytokines.
Figure 11:
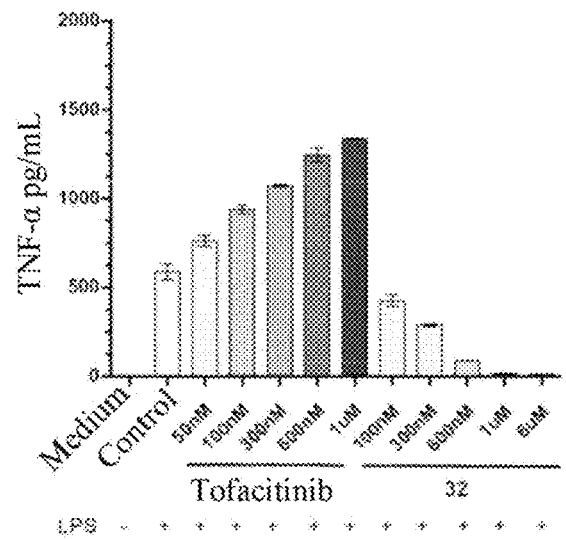
Figure 12:
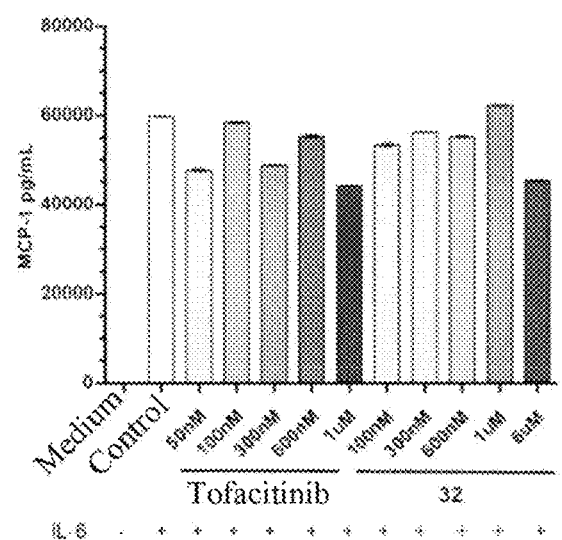

IL-6 stimulated inflammatory cytokine MCP-1 release assay was performed in a similar way. The experimental results are as shown in FIGS. 10-12.

In LPS-challenged PBMCs, the release of IL-6 and TNF-α was significantly inhibited by Compound 32. In contrast, the non-selective inhibitor Tofacitinib increased cytokine production in different degrees, because of the inhibition of IL-10-JAKs-STAT3 negative feedback signaling due to Tofacitinib's inhibition on JAK1. Compound 32 sustained IL-10 signal pathway function due to its selective inhibition on JAK3. Both Compound 32 and Tofacitinib did not inhibit IL-6-induced MCP-1 release (which is not mediated by JAKs), indicating that these two compounds adjust the release of inflammatory cytokines through the JAK-STAT signal pathway. These results demonstrated that Compound 32 selectively inhibits JAK3, and play an important role in modulating inflammatory cytokine release through inhibiting the JAK3-STATs signal pathway.

(7) Pharmacokinetics Evaluation

Pharmacokinetics (PKs) properties of Compound 32 in mice were evaluated following intravenous and oral administration.

For in vivo PKs study, male ICR mice (n=3) were fasted overnight and Compound 32 was received as an intravenous dose (2 mg/kg) or via oral gavage (5 mg/kg). Blood samples were collected at 0.08, 0.25, 0.5, 1, 2, 4, 8, and 24 h (iv) and 0.25, 0.5, 1, 2, 4, 8, and 24 h (po). The plasma samples were deproteinized with acetonitrile containing an internal standard. After centrifugation at 4° C., supernatants were collected for LC/MS/MS analysis.

The PKs were measured by the analysis of plasma concentrations at indicated time points. The results are shown in the table below. The data represents mean concentration in plasma (n=3), following a single 2.0 mg/kg intravenous dose and 5 mg/kg oral dose.

TABLE

| PKs Study of Compound 32 in ICR Mice | | |
|---|---|---|
| Compound 32 | iv (2 mg/kg) | po (5 mg/kg) |
| $AUC_{0-t}$ (ng · hr/mL) | 995 ± 181 | 578 ± 47 |
| $AUC_{0-\infty}$ (ng · hr/mL) | 997 ± 181 | 608 |
| $T_{1/2}$ (hr) | 0.44 ± 0.02 | 1.66 ± 1.06 |
| $V_z$ (L/kg) | 1.3 ± 0.21 | 18.8 ± 10.06 |
| Cl (mL min$^{-1}$ kg$^{-1}$) | 34.1 ± 5.62 | 138.47 ± 16.3 |
| MRT (hr) | 0.48 ± 0.05 | 1.51 ± 0.69 |
| Bioavailability (%) | | 24.4 |

Upon 5 mg/kg oral delivery, Compound 32 exhibited a PK profile with a half-life ($t_{1/2}$) of 1.66 h, area under curve (AUC) of 608 ng·hr/mL, and a moderate oral bioavailability of 24.4%. These potent PK properties suggested that Compound 32 could be an oral inhibitor or probe for further pharmacodynamics studies and biological function exploration in animals.

It should be understood that the embodiments above are for illustrative purpose only, and shall not constitute any limitation to the protection scope of the present invention. The protection scope of the present invention is determined by the appended claims, which include not only the literal interpretation of the technical solutions in the claims, but also the equivalents of the technical solutions in the claims. For example, stable isotope substitutes of compounds are also included in the protection scope of the present invention.

What is claimed is:

1. A compound of Formula I or a pharmaceutically acceptable salt thereof,

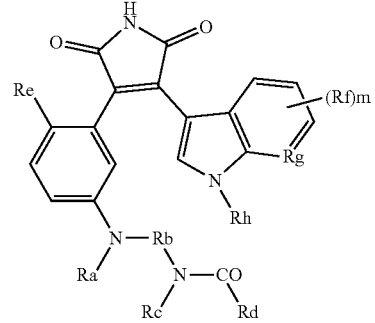

Formula I wherein,
Rh is H or methyl;
Rg is CH, —C—Rf or N;
Rf is a substituent;
m is 0, 1, 2 or 3;
Re is an electron-withdrawing group selected from the group consisting of tertiary amine cations, nitro, trihalomethyl, halogen, formyl, acyl, carboxyl, cyano and sulfonic acid group;
Rd is alkenyl or alkynyl;
Ra, Rb and Rc are selected from the group consisting of:
(1) Rb is $C_1$-$C_4$ alkylene, and
Ra and Rc are hydrogen or $C_1$-$C_6$ alkyl;
(2) Rb is $C_1$-$C_4$ alkylene, and
Ra and Rc are attached together to form $C_2$-$C_4$ alkylene;
(3) Ra is hydrogen or $C_1$-$C_6$ alkyl, and
Rb and Rc together with the N atom to which they are attached form a 5- or 6-membered saturated heterocyclic ring containing a N atom;

(4) Rc is hydrogen or $C_1$-$C_6$ alkyl, and

Ra and Rb together with the N atom to which they are attached form a 5- or 6-membered saturated heterocyclic ring containing a N atom.

2. The compound or a pharmaceutically acceptable salt thereof according to claim 1, wherein —N(Ra)-Rb-N(Rc)- forms

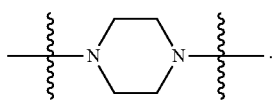

3. The compound or a pharmaceutically acceptable salt thereof according to claim 1, wherein Rh is H, Rg is CH, and m is 0.

4. The compound or a pharmaceutically acceptable salt thereof according to claim 1, wherein Re is —$NO_2$.

5. The compound or a pharmaceutically acceptable salt thereof according to claim 1, wherein Rd is vinyl.

6. A compound of Formula II or a pharmaceutically acceptable salt thereof:

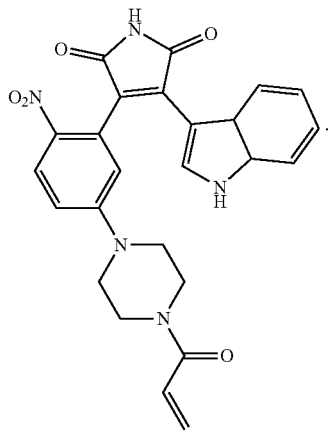

Formula II

7. A pharmaceutical composition comprising the compound of Formula I or a pharmaceutically acceptable salt thereof according to claim 1, and a pharmaceutically acceptable carrier.

8. A method of treating rheumatoid arthritis in a subject, comprising administering to the subject the compound of Formula I or a pharmaceutically acceptable salt thereof according to claim 1.

9. A compound selected from the group consisting of:

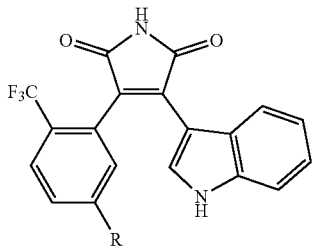

R =

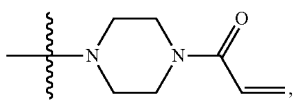 [SMILES: *N1CCN(C(=O)C=C)CC1]

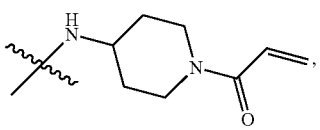 [SMILES: *NC1CCN(C(=O)C=C)CC1]

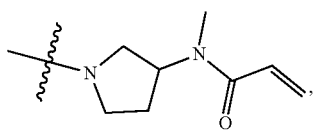 [SMILES: *N1CCC(N(C)C(=O)C=C)C1]

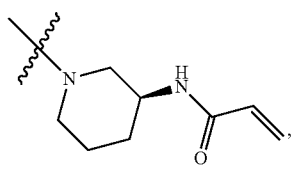 [SMILES: *N1CCC[C@H](NC(=O)C=C)C1]

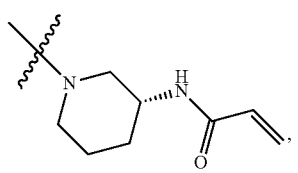 [SMILES: *N1CCC[C@@H](NC(=O)C=C)C1]

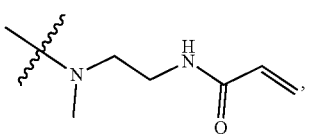 [SMILES: *N(C)CCNC(=O)C=C]

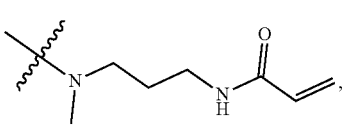 [SMILES: *N(C)CCCNC(=O)C=C]

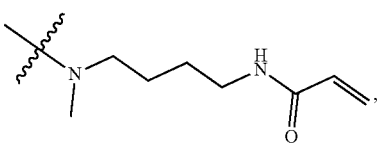 [SMILES: *N(C)CCCCNC(=O)C=C]

| 37 | 38 |
|---|---|
| 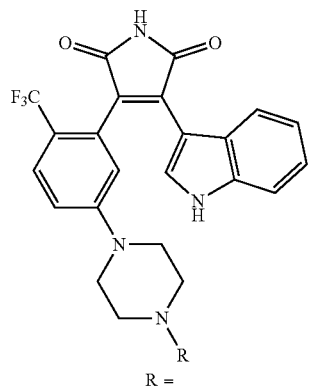 | -continued<br>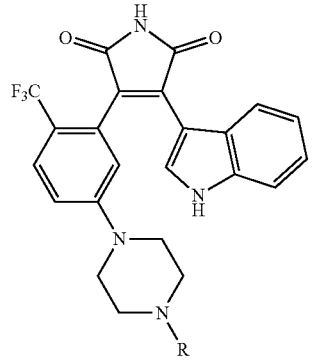 |
| R = | R = |
| 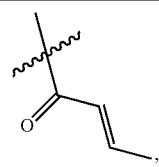 | 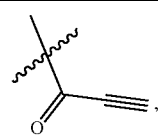 |
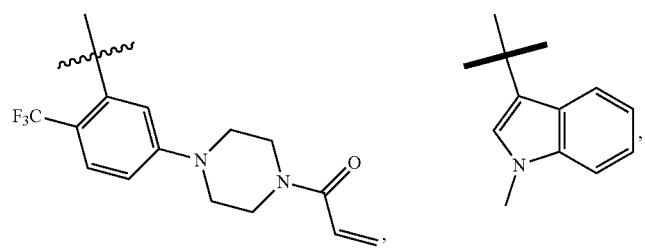
| R₁= | R₂= |
|---|---|
| 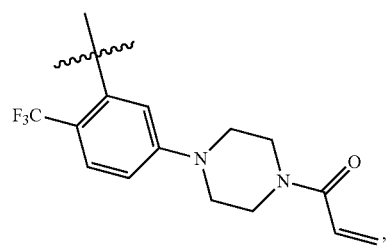 [SMILES: *c1cc(N2CCN(C(=O)C=C)CC2)ccc1C(F)(F)F] | 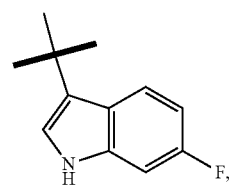 |
| 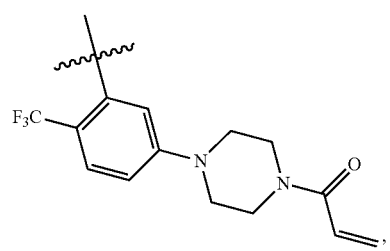 [SMILES: *c1cc(N2CCN(C(=O)C=C)CC2)ccc1C(F)(F)F] | 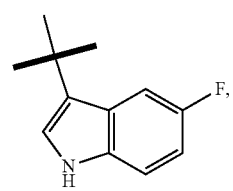 |

-continued
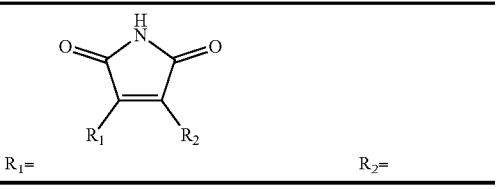
| R₁= | R₂= |
|---|---|
| 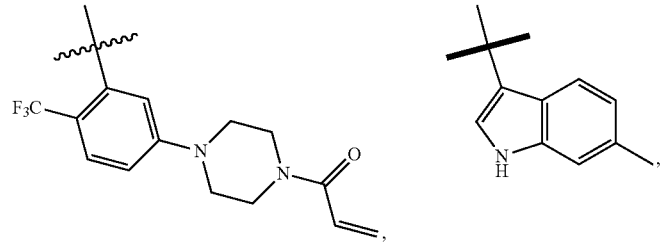 | |
| 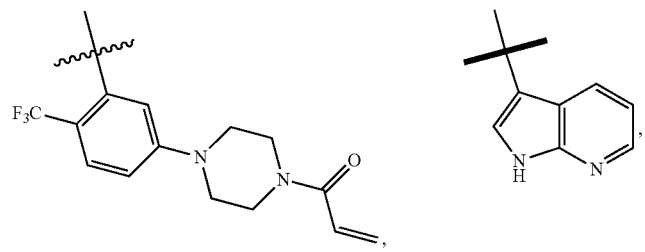 | |
| 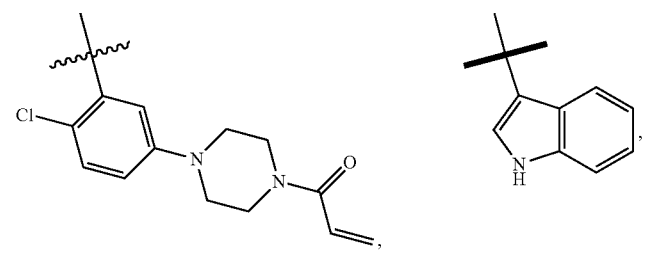 | |
| 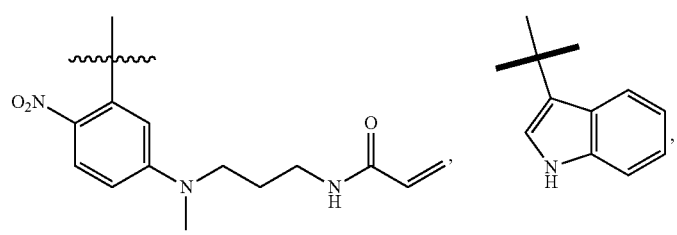 | |
| 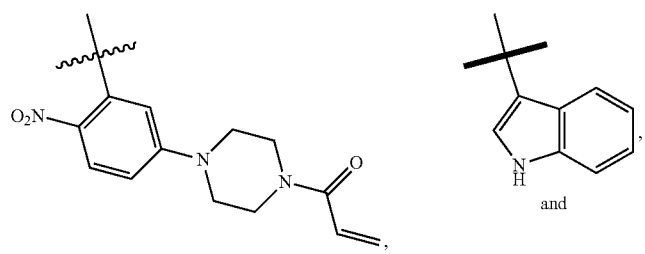 | and |
| 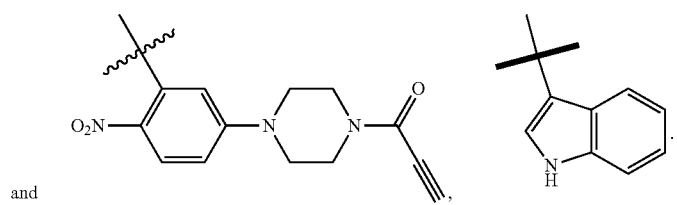 | |
and -continued

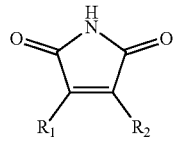

R₁=                                                    R₂=

10. The compound or a pharmaceutically acceptable salt thereof according to claim 2, wherein Rh is H, Rg is CH, and m is 0.

11. The compound or a pharmaceutically acceptable salt thereof according to claim 2, wherein Re is —NO$_2$.

12. The compound or a pharmaceutically acceptable salt thereof according to claim 3, wherein Re is —NO$_2$.

13. The compound or a pharmaceutically acceptable salt thereof according to claim 2, wherein Rd is vinyl.

14. The compound or a pharmaceutically acceptable salt thereof according to claim 3, wherein Rd is vinyl.

15. The compound or a pharmaceutically acceptable salt thereof according to claim 4, wherein Rd is vinyl.

16. A pharmaceutical composition comprising the compound of Formula II or a pharmaceutically acceptable salt thereof according to claim 6, and a pharmaceutically acceptable carrier.

17. A method of treating rheumatoid arthritis in a subject, comprising administering to the subject the compound of Formula II or a pharmaceutically acceptable salt thereof according to claim 6.

18. A method of treating rheumatoid arthritis in a subject, comprising administering to the subject the pharmaceutical composition according to claim 7.

19. The compound or a pharmaceutically acceptable salt thereof according to claim 1, wherein Rf is methyl or halogen; or Rd is alkenyl or alkynyl, having 2, 3, 4, 5 or 6 carbon atoms.

20. The compound or a pharmaceutically acceptable salt thereof according to claim 1, wherein Re is an electron-withdrawing group selected from the group consisting of
   (i) —N$^+$R'$_3$, wherein R' is independently selected from H and C$_1$-C$_6$ alkyl;
   (ii) —CX$_3$, wherein X is F, Cl, Br or I;
   (iii) F, Cl, Br or I; and
   (iv) —CO—C$_{1-4}$ alkyl.

\* \* \* \* \*